US006241995B1

(12) United States Patent
Estrada et al.

(10) Patent No.: US 6,241,995 B1
(45) Date of Patent: *Jun. 5, 2001

(54) *POLYGALA SENEGA* COMPOSITIONS AND METHODS OF USE

(75) Inventors: Alberto Estrada; Branka Barl; Georgios S. Katselis; Bernard Laarveld, all of Saskatoon (CA)

(73) Assignee: University of Saskatchewan, Saskatoon (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/130,397

(22) Filed: Aug. 6, 1998

Related U.S. Application Data

(63) Continuation-in-part of application No. 08/909,009, filed on Aug. 8, 1997, now abandoned.

(51) Int. Cl.[7] .............................. A61F 13/00; C09F 1/02
(52) U.S. Cl. ...................... 424/434; 424/435; 424/195.1; 424/278.1; 530/214
(58) Field of Search ................................. 424/434, 195.1, 424/435, 278.1; 530/214

(56) References Cited

U.S. PATENT DOCUMENTS

| 4,501,734 | * | 2/1985 | Tanaka et al. ........................ 514/198 |
| 5,057,540 |  | 10/1991 | Kensil et al. ........................... 514/25 |
| 5,700,787 | * | 12/1997 | Tzianabos et al. ..................... 514/54 |

FOREIGN PATENT DOCUMENTS

| 2 202 683A | 5/1974 | (FR) . |
| WO 88/09336 | 12/1988 | (WO) . |

OTHER PUBLICATIONS

Amoros et al., "in vitro Antiviral Acitivity of a Saponin from *Anagallis Arvensis*, Primulaceae, Against Herpes Simplex Virus and Polivirus," *Antiviral Res.* 8:13–25 (1987).
Anisimov et al., "Chemical Structure and Antifungal Activity of a Number of Triterpenoids," *Izv. Akad. Nauk SSSR, Ser. Biol. Chem.* Abstr. 107: 570–575, 108725 (1979).
Bhargava, S.K., "Antifertility Effects of *Sapindus Trifoliatus* L. Fruit Extract in Rats," *Int. J. Crude Drug Res.*26:229–233 (1988).
Chowdhury et al., "Biological Activity of the Alcohol Extract and the Glycosides of *Hydrocotile Asiatica*Linn.," *J. Bangladesh Academy Science*11:75–82 (1987).
Hostettmann, Kurt, "Saponins with Molluscicidal Activity from *Hedera Helix*L.," Helv. Chim. Acta. 63:606–609 (1980).
Hostettmann and Marston, 1995 in *Chemistry and Pharmacology of Natural Products: Saponins*(Phillipson, J.D., ed. Cambridge University Press, New York) p. 323.

Kako et al., "Effect of Senegin–II On Blood Glucose in Normal and NIDDM Mice," *Biol. Pharm. Bull.*18(8):1159–1161 (1995).
Kenarova et al., "Immunomodulating Acitivity of Ginsenoside RG from *Panax Ginseng*," *Japan J. Pharmacol.*54:447–454 (1990).
Kensil et al., "Separation and Characterization of Saponins with Adjuvant Activity from *Quillaja saponaria* Cortex," *The Journal Immunol.*146:431–437 (1991;.
Masuda et al., "Intraperitoneal Administration of Senegae Radix Extract and Its Main Component, Senegin–II, Affects Lipid Metabolism in Normal and Hyperlipidemic Mice," *Biol. Pharm. Bull.*19(2):315–317 (1996).
Mita et al., "Enhancement and Suppression of IgM–Antibody in Mice Treated With Purified Saponins," *Biomedicine*31(8):223–227 (1979).
Oleszek et al., "Isolation and Identification of Alfalfa (*Medicago sativa* L.) Root Saponins: Their Activity in Relation to a Fungal Bioassay," *J. Agric. Food Chem.*38:1810–1817 (1990).
Shibata, S., "Saponins with Biological and Pharmacological Activity," *New Natural Product and Plant Drugs with Pharmacological, Biological or Therapeutic Activity*(Wagner, H. And Wolff, P. Ed, Springer, Berlin) pp. 177–196 (1977).
So et al., "Effect of a Novel Saponin Adjuvant Derived From *Quillaja saponaria* on the Immune Response to Recombinant Hepatitis B Surface Antigen," *Mol. Cells*7(2):178–186 (1996).
Tsukitani et al., "Studies on the Constituents of Senegae Radix. III. The Structures of Senegin–II, Saponin from *Polygala senega* Linne var. *Latifolia* Torry et Gray," *Chem. Pharm. Bull.* 21(4):791–799 (1973).
Tsukitani ans Shoji, "Studies on the Constituents of Senegae Radix. III. The Structures of Senegin–III and –IV, Saponins from *Polygala senega* Linne var. *Latifolia* et Gray," Chem. Pharm. Bull. 21(7):1564–1574 (1973).
Yoshikawa et al., "Bioactive Saponins and Glycosides. Sengae Redix. (1): E–Senegasaponins a and b and Z–Senegasasaponins a and b, Their Inhibitory Effect on Alcohol Absorption and Hypoglycemic Activity," *Chem. Pharm. Bull.* 43(12):2115–2122 (1995).
Yoshikawa et al., "E–Senegasaponins a and b, Z–Senegasaponins a and b, Z–Senegins II and III, New Type Inhibitors of Ethanol Absorption in Rats from Senegae Radix, the Roots of *Polygala Senega*L. Var *Latifolia*Torrey et Gray," *Chem. Pharm. Bull.*43(2):350–352 (1995).
Program and Abstract–phytochemical Society of North America, Thirtieth Annual Meeting Aug. 10–14, 1996, Hotel Inter–Continental New Orleans, Louisana.
Yoshikawa et al. Chem. Pharm. Bull. 43(12) pp. 2115–2122, 1995.*

* cited by examiner

Primary Examiner—Thurman K. Page
Assistant Examiner—Lakshmi Channavajjala
(74) *Attorney, Agent, or Firm*—Robins & Associates

(57) ABSTRACT

Novel *Polygala senega* saponin pharmaceutical compositions are disclosed. The *P. senega* saponins are useful as immunological adjuvants to enhance immune responses to a co-administered antigen.

11 Claims, 15 Drawing Sheets

POLYGALA SENEGA COMPOSITIONS AND METHODS OF USE

CROSS-REFERENCE TO RELATED APPLICATION

This application is a continuation-in-part of U.S. patent application Ser. No. 08/909,009, filed Aug. 8, 1997, now abandoned, from which priority is claimed pursuant to 35 U.S.C. §120 and which application is incorporated herein by reference in its entirety.

TECHNICAL FIELD

The present invention relates generally to adjuvants for use in pharmaceutical compositions. In particular, the invention relates to *Polygala senega* saponin adjuvant compositions and methods of using the same.

BACKGROUND OF THE INVENTION

Many vaccine compositions include immunological adjuvants in order to increase antigenic potency. Immunological adjuvants act to augment cell-mediated and humoral immune responses. Such adjuvants include depot adjuvants, compounds which adsorb and/or precipitate administered antigens and which serve to retain the antigen at the injection site. Typical depot adjuvants include aluminum compounds and water-in-oil emulsions. However, depot adjuvants, although increasing antigenicity, often provoke severe persistent local reactions, such as granulomas, abscesses and scarring, when injected subcutaneously or intramuscularly. Other adjuvants, such as lipopolysacharrides and muramyl dipeptides, can elicit pyrogenic responses upon injection and/or Reiter's symptoms (influenza-like symptoms, generalized joint discomfort and sometimes anterior uveitis, arthritis and urethritis). Accordingly, there is a continued need for effective and safe adjuvants for use in a variety of pharmaceutical compositions.

Saponins are high molecular weight, glycosidic, natural plant surfactants, consisting of an aglycone ring linked to one or more sugar chains. Although saponins share common properties, they are structurally diverse. For example, the aglycone can be steroid, triterpenoid or a steroidalalkaloid and the number of sugars attached to the glycosidic bonds varies greatly.

Numerous pharmacological properties have been attributed to saponins, including anti-inflammatory (Shibata, S. (1977) in *New Natural Products and Plant Drugs with Pharmacological, Biological or Therapeutic Activity* (Wagner, H. and Wolff, P. eds, Springer, Berlin) pp. 177–196); antiviral (Amoros et al., *Antiviral Res.* (1987) 8:13–25); molluscicidal (Hostettmann, K., Helv. *Chim. Acta.* (1980) 63:606–609); contraceptive (Bhargava, S. K., *Int. J. Crude Drug Res.* (1988) 26:229–233); antibacterial (Chowdhury et al., *J. Bangladesh Acad. Sci.* (1987) 11:75–82); and fungicidal activities (Anisimov et al., *Izv. Akad. nauk SSSR, Ser. Biol.* (1979), 570–575 (Chem. Abstr. 107:108725).

More recently, saponins have been found to exhibit adjuvant and immunostimulating properties. See, e.g., Kensil et al., *J. Immunol.* (1991) 146:431–437. For example, the triterpene glycoside saponins extracted from the South American tree, *Quillaja saponaria*, termed Quil A (U.S. Pat. No. 5,057,540; International Publication No. WO 88/09336, published Dec. 1, 1988) have been used as immunological adjuvants in vaccine compositions against a variety of infectious diseases.

Roots of the plant Polygala senega (commonly known as "snakeroot"), contain at least 6–10 triterpenoid saponins. Hostettmann and Marston, 1995 in *Chemistry and Pharmacology of Natural Products: Saponins* (Phillipson, J. D., ed. Cambridge University Press, New York) p. 323, the main saponins being senegin II, III and IV (Shoji et al., *Chem. Pharm. Bull.* (1973) 21:791–799; Tsukitani and Shoji, *Chem. Pharm. Bull.* (1973) 21:1564–1574; and Yoshikawa et al., *Chem. Pharm. Bull.* (1995) 43:350–352. These saponins differ from Quil A saponins in (a) the number of sugars present in the side chains of the molecules, and (b) the presence of different functional groups in the triterpenoid aglycone. Thus, the *P. senega* saponins are chemically distinct from the *Quillaja saponaria* saponins.

*P. senega* saponins have been reported to exhibit hypoglycemic effects (Kako, et al., *Biol. Pharm. Bull.* (1995) 18:1159–1161 and Yoshikawa et al., *Chem. Pharm. Bull.* (1995) 43:2115–2122); reduce blood triglyceride levels (Masuda et al., *Biol. Pharm. Bull.* (1996) 19:315–317); and reduce alcohol absorption (Yoshikawa et al., *Chem. Pharm. Bull.* (1995) 43:350–352 and Yoshikawa et al., *Chem. Pharm. Bull.* (1995) 43:2115–2122). However, the use of Polygala senega saponins as immunological adjuvants has not been previously described.

DISCLOSURE OF THE INVENTION

The present invention is based on the surprising discovery that *P. senega* saponins are able to act as immunological adjuvants to enhance immune responses to a co-administered antigen.

In one embodiment, the subject invention is directed to a composition comprising:

(a) a *P. senega* saponin extract comprising at least one *P. senega* saponin capable of potentiating an immunological response;

(b) a selected antigen; and (c) a pharmaceutically acceptable vehicle.

In another embodiment, the invention is directed to a composition comprising:

(a) a *P. senega* saponin extract comprising at least one *P. senega* saponin capable of potentiating an immunological response, wherein said *P. senega* saponin extract is obtained by a method comprising:
  (i) providing roots of a *P. senega* L plant;
  (ii) extracting a crude saponin mixture from the roots with methanol;
  (iii) extracting the crude mixture from (ii) with n-butanol;
  (iv) performing column chromatography on the butanolic extract; and
  (v) obtaining fractions from step (iv) with hemolytic activity;

(b) a selected antigen; and (c) a pharmaceutically acceptable vehicle.

In other embodiments, the invention is directed to methods for stimulating an immunological response in a vertebrate subject. The methods comprise administering an effective amount of the pharmaceutical compositions above to the subject.

In another embodiment, the invention is directed to a method for stimulating an immunological response in a vertebrate subject, wherein the *P. senega* saponin, comprising at least one *P. senega* saponin capable of potentiating an immunological response, can be administered with the antigen or administered in a separate composition.

In still a further embodiment, the invention is directed to a method of making a composition. The method comprises combining a *P. senega* saponin extract comprising at least one *P. senega* saponin capable of potentiating an immunological response, with a selected antigen.

These and other embodiments of the present invention will readily occur to those of ordinary skill in the art in view of the disclosure herein.

DETAILED DESCRIPTION OF THE INVENTION

Figure 1:
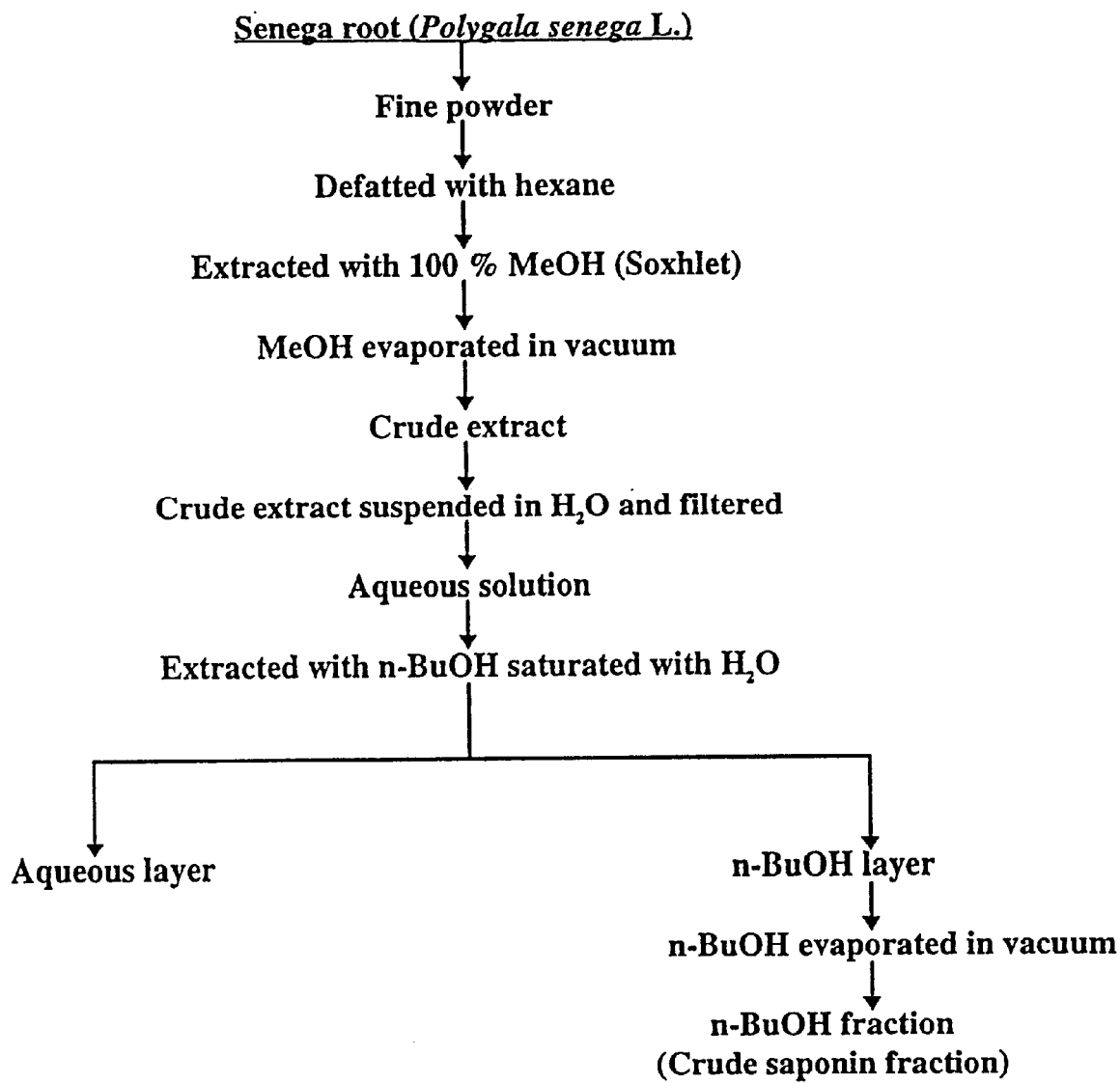
FIG. 1 depicts the scheme used to extract saponins from *P. senega* root.

The practice of the present invention will employ, unless otherwise indicated, conventional methods of chemistry, biochemistry, immunology and pharmacology, within the skill of the art. Such techniques are explained fully in the literature. See, e.g., *Remington's Pharmaceutical Sciences*. 18 $^{th}$ Edition (Easton, Pa.: Mack Publishing Company, 1990); *Methods In Enzymology* (S. Colowick and N. Kaplan, eds., Academic Press, Inc.); and, *Handbook of Experimental Immunology*, Vols. I–IV (D. M. Weir and C. C. Blackwell, eds., 1986, Blackwell Scientific Publications).

All publications, patents and patent applications cited herein, whether supra or infra, are hereby incorporated by reference in their entirety. As used in this specification and the appended claims, the singular forms "a," "an" and "the" include plural references unless the content clearly dictates otherwise. Thus, the term "a saponin" can include more than one saponin or even a crude extract comprising several saponins.

A. Definitions

In describing the present invention, the following terms will be employed, and are intended to be defined as indicated below.

By "*Polygala senega* saponin extract" is meant a composition comprising one or more of the various sapogenin glycosides derived from the *P. senega* plant, as well as isomers or derivatives thereof, which individually or in combination act as immunological adjuvants, for enhancing non-specific immunity, as well as enhancing the action of an antigen co-administered therewith. The term encompasses crude saponin extracts which contain all or most of the saponins present in a given *P. senega* plant, as well as partially purified and highly purified saponins derived from *P. senega*. The term "extract" as used herein refers to both liquid and solid forms (e.g., by the elimination of the solvent) of one or more of the *P. senega* saponins. Immunological adjuvant activity of the *P. senega* saponins can be tested using standard techniques including ELISAs, hemagglutination assays, neutralization assays and the like.

The term encompasses extracts containing one or more saponins derived from any of the several varieties of *P. senega*, including without limitation, *P. senega* L., a plant indigenous to Manitoba and Saskatchewan Canada; *P. senega* L. var. *latifolia* Torry et Gray, cultivated in Japan; and *P. senega*, var. *typica*. Examples of specific saponins include, without limitation, those derived as described herein, as well as the glycosides derived from *P. senega* L. var. *latifolia* Torry et Gray, known as senegin I; senegin II ($C_{70}H_{104}O_{32}$·$4H_2O$, presenegin bonded with rhamnose, fucose, xylose, galactose, glucose and 3,4-dimethoxycinnamic acid, see below); senegin III ($C_{69}H_{102}O_{31}$·$4H_2O$, presenegin bonded with rhamnose, fucose, galactose, glucose and 4-methoxycinnamic acid, see below); senegin IV ($C_{75}H_{112}O_{35}$·$4H_2O$, presenegin bonded with 2 moles of rhamnose, fucose, xylose, galactose, glucose and 4-methoxycinnamic acid). See, e.g., Shoji et al., *Yakugaku Zasshi* (1971) 91:198–202; Tsukitani and Shoji, *Chem. Pharm. Bull.* (1973) 21:1564–1574; Tsukitani et al., *Chem. Pharm. Bull.* (1973) 21:791–799. Other saponins derived from *P. senega* L. var. *latifolia* Torry et Gray include E-senegasaponins a and b; the Z-senegasaponins a and b; the Z-senegins II and III; desacylsenegasaponin a; desacylsenegin II and desacylsenegin III. See, e.g., Yoshikawa et al., *Chem. Pharm. Bull.* (1995) 43:350–352; Yoshikawa et al., *Chem. Pharm. Bull.* (1995) 43:2115–2122.

Saponins derived from *P. senega* var. *typica* will also find use with the present invention and include saponin A, B, C, D, E, A', B' and C' (preseegenin bonded with glucose, galactose, xylose, fucose and rhamnose molecules present in amounts as follows: 3,1,2,1,1 (saponin A); 2,1,1,1,1 (saponin B); 2,1,1,1,1 (saponin C); 3,1,1,0,1 (saponin D); 3,0,1,1,1 (saponin E); 3,1,1,1,2 (saponin A'); 1,1,1,1,1 (saponin B'); and 3,1,0,0,1 (saponin C'). See, e.g., Brieskorn and Renke, *Deut. Apoth. Zig.* (1968) 108:1601.

Preferred saponins are represented by the general structure:

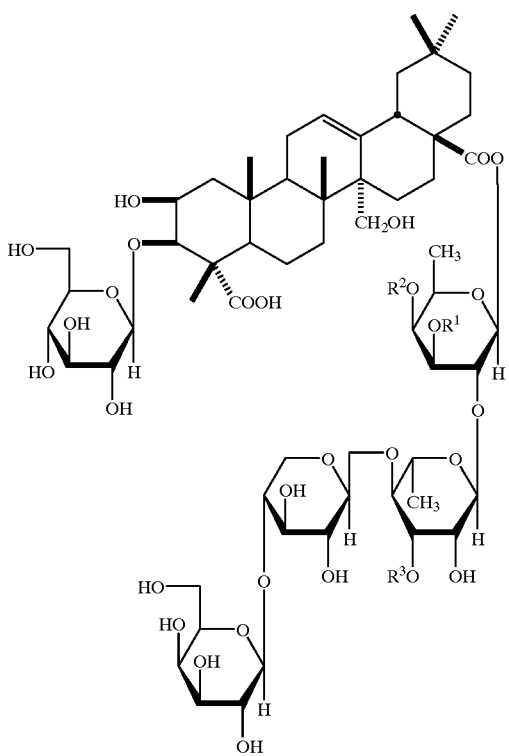

where $R^1$ is selected from the group consisting of hydrogen and α-L-rhamnopyranosyl; $R^2$ is selected from the group consisting of hydrogen, the E isomer of 4-methoxycinnamoyl, the Z isomer 4-methoxycinnamoyl, the E isomer of 3,4-dimethoxycinnamoyl, the Z isomer of 3,4-dimethoxycinnamoyl; and $R^3$ is selected from the group consisting of hydrogen and β-D-apiofuranosyl. Examples of particular saponins having this general formula are given in Table 1.

TABLE 1

| Saponin | $R^1$ | $R^2$ | $R^3$ |
| --- | --- | --- | --- |
| E-senegasaponin a: | H | E-MC | Api |
| Z-senegasaponin a: | H | Z-MC | Api |
| desacylsenegasaponin a: | H | H | Api |
| E-senegasaponin b: | H | E-MC | H |
| Z-senegasaponin b: | H | Z-MC | H |
| senegin II: | H | E-DMC | H |
| Z-senegin II: | H | Z-DMC | H |
| desacylsenegin II: | H | H | H |
| senegin III: | Rha | E-MC | H |
| Z-senegin III: | Rha | Z-MC | H |
| desacylsenegin III: | Rha | H | H |

MC: 4-methoxycinnamoyl
DMC: 3,4-dimethoxycinnamoyl
Api: β-D-apiofuranosyl
Rha: α-L-rhamnopyranosyl An "antigen" refers to a molecule containing one or more epitopes that will stimulate a host's immune system to make a secretory, humoral and/or cellular immunological response. The term denotes both, subunit antigens, i.e., antigens which are separate and discrete from a whole organism with which the antigen is associated in nature, as well as killed, attenuated or inactivated bacteria, viruses, parasites or other microbes. Antibodies such as anti-idiotype antibodies, or fragments thereof, and synthetic peptides, which can mimic an antigen or antigenic determinant are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

An "immunological response" to a pharmaceutical composition according to the present invention is the development in the host of a secretory, cellular and/or antibody-mediated immune response to the composition of interest. Usually, such a response includes but is not limited to one or more of the following effects; the production of antibodies from any of the immunological classes, such as immunoglobulins G, M, A, D or E; the proliferation of B and T lymphocytes; the activation, growth and differentiation signals to immune cells; expansion of T helper, T suppressor and/or T cytotoxic lymphocytes. Generally, the foregoing events will be substantially directed toward an antigen or antigens included in the composition of interest. However, as described further below, the saponin compositions of the present invention can also be used to enhance non-specific immunostimulatory activities and such is included in the definition of "immunological response" as used herein.

An "immunological adjuvant" refers to a composition containing a *P. senega* saponin or a *P. senega* saponin extract, which potentiates an immunological response in the subject to which it is administered. The *P. senega* saponin can be incorporated into or administered with the antigen or administered in a separate composition. Alternatively, the *P. senega* saponin can be administered without an accompanying antigen to stimulate non-specific immunity. An immunological adjuvant may enhance the immunological response by making the antigen more strongly immunogenic or by lowering the dose of antigen necessary to achieve an immune response in the subject to which it is administered.

A pharmaceutical composition which contains a *P. senega* saponin and a selected antigen pursuant to the present invention displays "enhanced immunogenicity" when it possesses a greater capacity to elicit an immune response than the immune response elicited by the corresponding antigen when administered without the *P. senega* saponins. Such enhanced immunogenicity can be determined by administering the saponin composition and antigen controls to animals and comparing antibody titers against the two using standard assays such as radioimmunoassay and ELISA, well known in the art.

For purposes of the present invention, "an effective amount" of a *P. senega* saponin will be that amount which enhances an immune response to a co-administered antigen, or an amount of a *P. senega* saponin which stimulates non-specific immunity when no antigen is present.

By "pharmaceutically acceptable" is meant a material which is not biologically or otherwise undesirable, i.e., the material may be administered to an individual along with the selected adjuvant formulation without causing any undesirable biological effects or interacting in a deleterious manner with any of the components of the pharmaceutical composition in which it is contained.

By "vertebrate subject" is meant any member of the subphylum chordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are intended to be covered.

B. General Methods

Central to the present invention is the discovery that *P. senega* saponin compositions can promote production of immunoglobulin G (IgG) and the subclasses $IgG_1$ and $IgG_{2a}$. *P. senega* saponin compositions also induce the production of interleukins and interferon-gamma (IFN-γ) by lymphocytes. Thus, *P. senega* saponins enhance both humoral and cellular immune responses in a vertebrate subject when administered with a selected antigen. Additionally, the *P. senega* saponins may be used to enhance non-specific immunity.

Systemic antibodies, such as serum IgG, play a significant role in neutralizing infectivity of invading organisms and promoting aggregation and clearance of pathogens, such as bacteria and viruses. Thus, the ability of the *P. senega* saponins to augment both IgG and cytokine production against selected antigens provides a powerful tool against infection by a wide variety of organisms.

Accordingly, as is evident, the *P. senega* saponins can be used as immunological adjuvants in vaccine compositions for a variety of purposes. For example, the *P. senega* saponins can be used in compositions for immunizing a vertebrate subject against a selected pathogen or against a subunit antigen derived therefrom, or for priming an immune response to a particular antigen or, for example, stimulating an immune response against a desired hormone, e.g., for reproductive purposes such as fertility control and immunological sterilization. The compositions can also be used to stimulate non-specific immunity. If used for this purpose, a specific antigen need not be present or co-administered with the *P. senega* saponin adjuvants.

Antigens when administered with the *P. senega* pharmaceutical compositions, can be derived from a wide variety of viruses, bacteria, fungi, plants, protozoans and other parasites. Such antigens can be derived from, e.g., any of the various species of Pasteurella, Actinobacillus, Haemophilus, Salmonella, Eimeria, and the like, as well as viruses including, e.g., rotaviruses, herpesviruses, parvovirus, rabies virus, influenza viruses, parainfluenza viruses, hepatitis viruses, HIV, coronaviruses and the like. Similarly, antibody responses to tumor antigens, hormones, hormone analogs, and so forth, will also be enhanced by use of the *P. senega* compositions herein described.

The antigen can be a protein, polypeptide, antigenic protein fragment, oligosaccharide, polysaccharide, or the like. Similarly, an oligonucleotide or polynucleotide, encoding a desired antigen, can be administered with the *P. senega* saponin adjuvants for in vivo expression.

Antibodies such as anti-idiotype antibodies, or fragments thereof, can also be used in conjunction with the *P. senega* adjuvants. Furthermore, the *P. senega* adjuvants can be used in combination with antibodies for passive immunization.

The *P. senega* saponin pharmaceutical compositions will often contain the antigen or drug of interest, either free or complexed to the saponin, as described in European Patent Application No. 244,719, published Nov. 11, 1987 and International Publication No. WO 93/05789, published Apr. 1, 1993. However, the antigen or drug need not be present in the saponin composition but can be administered separately, either simultaneously, just prior to or subsequent to the saponin composition.

*P. senega* saponins for use in the pharmaceutical compositions of the present invention can be purified from the *P. senega* plant using methods well known in the art. See, e.g., Masuda et al., *Biol. Pharm. Bull.* (1996) 19:315–317; Shoji et al., *Yakugaku Zasshi* (1971) 91:198–202; Yoshikawa et al., *Chem. Pharm. Bull.* (1995) 43:2115–2122. A particularly preferred method for obtaining saponins from *P. senega* involves an alcohol extraction of the root of the plant, as shown in FIG. 1. Generally, plant roots are first dried and ground into a fine powder and defatted with an appropriate agent such as any lipid solvent, for example, hexane. A crude extract is then obtained using a polar alcohol, such as methanol (MeOH). Following extraction, the alcohol is evaporated and the crude extract can be suspended in water, centrifuged to remove any undissolved substances and filtered. The product can be further extracted with an alcohol such as n-butanol (n-BuOH) saturated with water. The upper alcoholic layer, containing saponins, is then evaporated under vacuum to give a crude saponin fraction.

The extracted saponins can be used as is or further purified using such techniques as column chromatography, HPLC and affinity chromatography.

Figure 2:
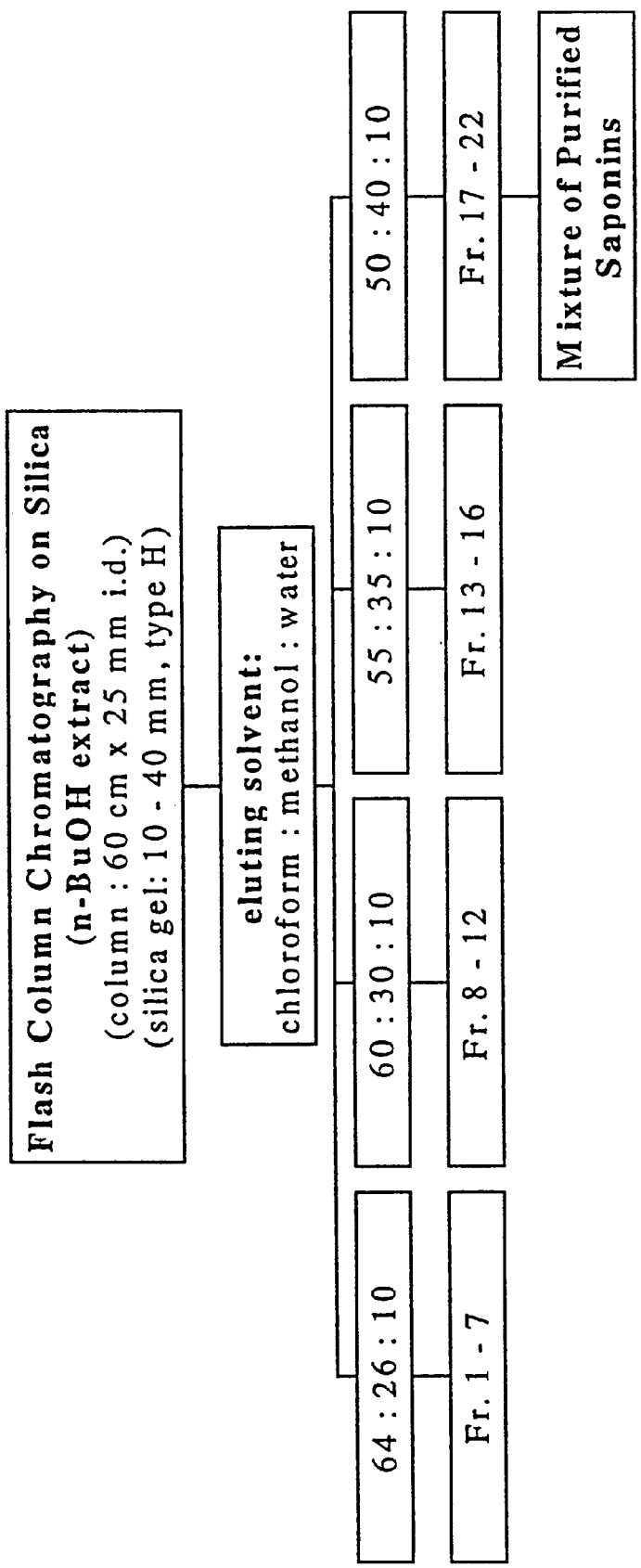
FIG. 2 depicts the flash column chromatography scheme used in saponin isolation and purification.

For example, the crude extract can be further purified using, e.g., column chromatography that employs a matrix which is not susceptible to degradation by organic solvents. A particularly suitable matrix is a silica matrix with particle sizes of about 10–40 µm, such as the type H silica matrix available from Sigma, St. Louis, Mo. One method for further purifying the crude extract is shown in FIG. 2. In this method, the dried butanolic extract is dissolved in a minimal amount of chloroform ($CHCl_3$)/methanol (MeOH)/water ($H_2O$) and applied to the silica gel. The column is then eluted with a solvent gradient of chloroform ($CHCl_3$)/methanol (MeOH)/water ($H_2O$). Eluted fractions are monitored for saponin activity using hemolytic assays, as described further below.

Following extraction of the *P. senega* saponins, it may be desirable to complex the saponins with a sterol and, optionally, a phospholipid, to produce immunostimulating complexes known in the art as ISCOMs. ISCOMs have been shown to enhance absorption, pharmacological activity and tolerability of saponin adjuvants. Useful sterols include, for example, cholesterol, β-sitosterol, lanosterol, lumisterol, stigmasterol and sitosterol. Useful phospholipids include, for example, phosphatidic acid and esters thereof including phosphatidylcholine and phosphatidylethanolamine. Methods for producing ISCOMs are known in the art and described in e.g., U.S. Pat. No. 5,118,671, U.S. Pat. No. 4,900,549, International Publication No. WO 90/03184 and Bomford et al., *Vaccine* (1992) 10:572–577.

The *P. senega* saponins, in the form of a crude extract, a more purified product, or as ISCOMs, are then formulated into pharmaceutical compositions. Such compositions will contain an effective amount (as defined above) of the *P. senega* saponins. The appropriate amounts of the saponins to be administered will depend on the mode of administration and can be readily determined by one skilled in the art based on activity assays of the preparations, such as hemolytic activity assays, as described in the examples. For example, if the compositions are administered parenterally, generally, from about 0.1 to about 1000 hemolytic units (HU) will be delivered, more particularly from about 1 to about 200 HU and most preferably from about 5 to about 100 HU. For oral delivery, generally from about 10 to about 100,000 HU will be administered, more particularly from about 50 to about 10,000 HU and most preferably from about 100 to about 1000 HU. Doses for other modes of administration can be readily determined by one of skill in the art.

The *P. senega* saponin compositions will generally include a compatible pharmaceutical vehicle, such as, for example, water, saline, dextrose, glycerol, ethanol, or the like, and combinations thereof. The pharmaceutical compositions may additionally contain biological buffers, preservatives, wetting and emulsifying agents, and the like. The formulations may also include other adjuvants, in addition to the *P. senega* saponins, including for example, other saponins, muramyl dipeptides, avridine, aluminum hydroxide, oils, cytokines, and other substances known in the art. A particularly preferred adjuvant in addition to the *P. senega* saponin composition is the triterpene glycoside saponin extracted from the South American tree, *Quillaja saponaria*, termed Quil A (U.S. Pat. No. 5,057,540; International Publication No. WO 88/09336, published Dec. 1, 1988).

As explained above, the *P. senega* saponin compositions may or may not contain an antigen or other substance of interest. For example, formulations may be administered without an antigen, so as to induce a non-specific immunostimulatory response. Similarly, an antigen or drug composition can be administered separately from the *P. senega* saponin compositions. A selected antigen, if included in the composition, will be present on the order of about 0.1 $\mu$g to about 1000 $\mu$g, more preferably about 1 $\mu$g to about 100 $\mu$g. Other amounts which are effective for eliciting an immune response will also be useful in the present compositions. If a drug is included in the composition, the amount present will depend on the type of drug used and is readily determined by one of skill in the art.

Some antigens or drugs will benefit by being coupled with a carrier molecule. This is particularly true of small peptides, such as small peptide hormones or substances with short half-lives and poor immunogenicity. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; inactive virus particles; and polynucleotides.

The mode of administration of the *P. senega* saponin compositions will vary according to the intended use. For example, if used as immunological adjuvants (e.g., in the case of a vaccine) and systemic immunity is required, the *P. senega* saponin compositions will generally be administered parenterally, usually by subcutaneous or intramuscular injection. If mucosal immunity is required, the *P. senega* saponin will generally be administered enterally, usually by oral dosing or inhalation. Other modes of administration, however, such as intradermal, intraperitoneal and intravenous injections, are also acceptable. The subject is immunized by administration of at least one dose, and preferably two or more doses. Moreover, the subject may be administered as many doses as is required to enhance immunity to the pathogen in question.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

C. Experimental

EXAMPLE 1

Isolation and Purification of *P. Senega* Saponins

*P. senega* saponins were extracted from roots using 100% methanol (MeOH) and a Soxhlet apparatus. FIGS. 1 and 2 show a schematic representation of the isolation-purification procedure. Dry roots from *P. senega* L. were ground into a fine powder, defatted in hexane and extracted with MeOH. A brown syrup-like, crude extract was obtained upon evaporation of MeOH and was freeze-dried.

The crude extract was suspended in water and centrifuged (Beckman J2–21M/E; 10,000 rpm, 15 min) to remove any undissolved substances. The supernatant was filtered (Whatman f.p. 202 grade) and extracted with n-butanol (n-BuOH) saturated with water. The upper butanolic layer, containing saponins, was evaporated under vacuum to give a crude butanolic extract (2.5%).

As shown in FIG. 2, open column chromatography (flash chromatography) was used to further purify the crude extract. The column (60 cm-length; 25 mm-internal diameter) was packed with a slurry of silica gel (10–40 $\mu$m, type H, Sigma, St. Louis, Mo.) in chloroform ($CHCl_3$)/methanol (MeOH)/water ($H_2O$) (64/26/10, lower phase). The dried butanolic extract was dissolved in a minimal amount of chloroform ($CHCl_3$)/methanol (MeOH)/water ($H_2O$) (64/26/10, lower phase) and applied with a pipette to the top of the silica gel. The column was subsequently eluted with a solvent gradient of chloroform ($CHCl_3$)/methanol (MeOH)/water ($H_2O$) (64/26/10, 60/30/10, 55/35/10, 50/40/10, lower phases). A total of 22 fractions were collected consisting of 15 ml each. Fractions 1–7 were collected with the first solvent gradient; fractions 8–12 with the second; fractions 13–16 with the third; and fractions 17–22 with the fourth solvent gradient.

All eluted fractions were analysed by thin layer chromatography (TLC) using n-butanol:acetic acid:water (40:10:50; upper phase) (Wagner et al., *Plant Drug Analysis: A Thin Layer Chromatography Atlas*, pp. 225–245. Springer-Verlag, New York). The developed plates were air-dried, observed under UV light and sprayed with the anisaldehyde-sulphuric acid reagent (ASR) (Wagner et al., supra). Bands were visualized after color development upon heating.

Fractions 17–22 contained a mixture of purified saponins. Fractions 17 and 19 were used for the immunological studies (below) and designated as *P. senega* fractions 1 and 2, respectively. *P. senega* fractions 1 and 2 were further analysed by high-performance liquid chromatography (HPLC).

Figure 3:
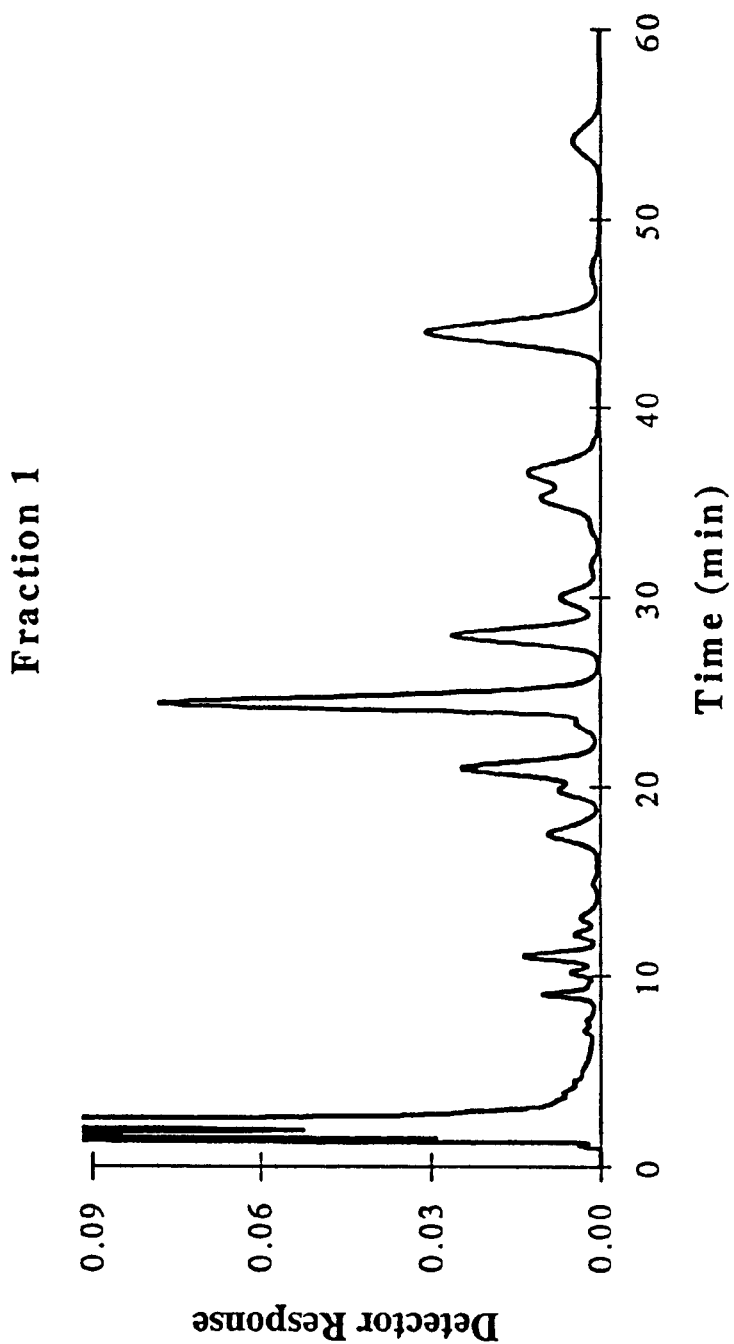
FIG. 3 depicts a chromatogram of *P. senega* fraction 1, as described in the examples.
Figure 4:
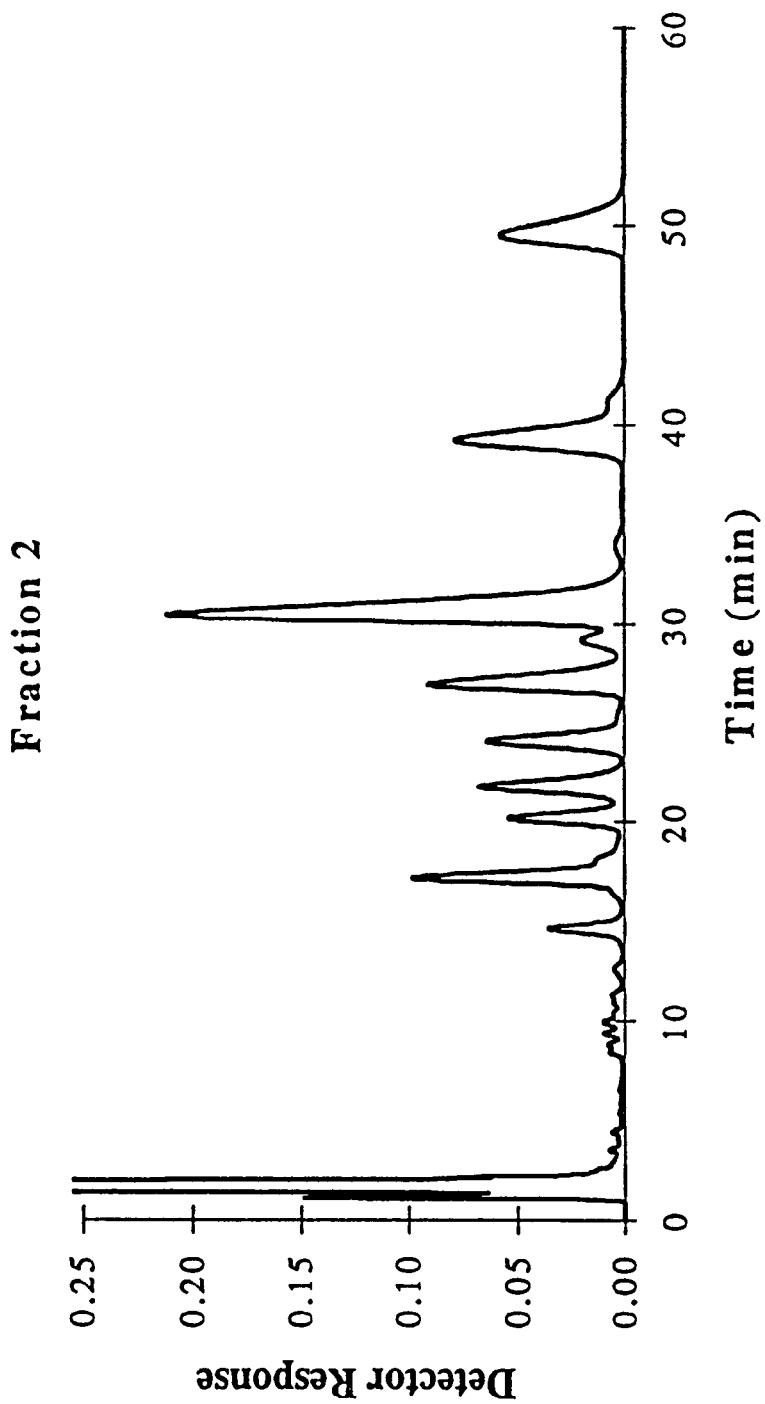
FIG. 4 depicts a chromatogram of *P. senega* fraction 2, as described in the examples.

FIGS. 3 and 4 illustrate the HPLC profile of *P. senega* fractions 1 and 2. FIG. 3 is a chromatogram of *P. senega* fraction 1. The column used was a Waters Nova-Pak® 60 Å 4 $\mu$m (15 cm×3.9 mm) i.d.) $C_{18}$; eluant, 25% solvent A [10% ammonium acetate buffer (pH 6.9, 50 mM)—90% acetonitrile] and 75% solvent B [90% ammonium acetate buffer (pH 6.9, 50 mM)—10% acetonitrile]; flow rate, 1 mL/min; detection at 315 nm.

FIG. 4 is a chromatogram of *P. senega* fraction 2. The column used was a Waters Nova-Pak® 60 Å 4 $\mu$m (15 cm×3.9 mm) i.d.) $C_{18}$; eluant, 25% solvent A [10% ammonium acetate buffer (pH 6.9, 50 mM)—90% acetonitrile] and 75% solvent B [90% ammonium acetate buffer (pH 6.9, 50 mM)—10% acetonitrile]; flow rate, 1 mL/min; detection at 315 nm.

Since saponins are known to lyse red blood cells, an hemolytic test was used to test the activity of the *P. senega* saponins as follows. Quil A saponins from *Quillaja saponaria*, obtained from Superfos Biosector, edbaek, Denmark, and used in the experiments below, were also tested for activity using this method. 100 microliters of 2% sheep red blood cells in phosphate-buffered saline (PBS) were added to individual wells of a 96 well microtiter plate. One mg of the saponins in PBS were added to the top wells and double dilutions were performed. The saponin content was estimated as the last dilution presenting complete hemolysis of the red cells and expressed as hemolytic units (HU) per mg of material. The hemolytic activity of Quil A, *P. senega* fraction 1 and *P. senega* fraction 2 saponins were 128, 32 and 64 HU per mg, respectively.

Infrared spectra were also taken on the fractions using a Bio-Rad FTS 40 infrared spectrometer. Samples were suspended in potassium bromide (KBr). The infrared spectrum of fraction 17 indicated the presence of many hydroxyl groups (broad peak at 3410 $cm^{-1}$), the presence of ester groups at 1720 $cm^{-1}$, a double bond at 1631 $cm^{-1}$ and a benzene system at 1513 $cm^{-1}$. The hydroxyl groups are present in the aglycon and also in the sugars in the side chains, the ester groups represent the linkage between the aglycon and the sugar side chain and the benzene is part of the chromophore.

Mass spectra were obtained for the fractions above by Fast Atom Bombardment (FAB) using Fisions 70SE mass spectrometer operating in the negative mode with a cesium (Cs) source. Samples were suspended in glycerol, which served as the matrix. Fractions 17 and 18 gave a strong base peak at m/z 1455 $(M-H)^-$, fraction 19 at m/z 1588 $(M-H)^-$, fraction 20 at m/z 1571 $(M-H)^-$, and fraction 21 at m/z 1704 $(M-H)^-$. The ions at m/z 1455 and 1571 $(M-H)^-$ corresponded to saponins isolated from *P. senega* L. var. *latifolia* Torry et Gray (Shoji et al., *Chem. Pharm. Bull.* (1973) 21:791–799; Tsukitani and Shoji, *Chem. Pharm. Bull.* (1973) 21:1564–1574; Yoshikawa et al., *Chem. Pharm. Bull.* (1995) 43:350–352), namely senegin II and III, respectively.

NMR data on the fractions were obtained using an $^1$H-NMR Bruker AM-300 spectrometer. Samples were dissolved in deuterated methanol. The NMR results demonstrated the complex nature of the saponin fractions. Signals at 4 ppm and in the region of 5 to 6 ppm, from MNR spectrum of fraction 18, were indicative of a vinyl proton, due to a double bond in the aglycon, and of multiple signals from the anomeric protons of the sugar moieties, respectively.

EXAMPLE 2

Adjuvant Activity of *P. Senega* Saponins

To examine the adjuvant activity of *P. senega* saponins in vivo, the primary and secondary immune responses of mice to saponins were measured. Responses to Quil A saponins were also measured for comparison.

CD-1 mice were obtained from the Animal Resources Centre, University of Saskatchewan (Saskatoon, Canada). The mice were 6–8 weeks of age when first used. Ovalbumin (OVA) (Sigma Chemical Co., St. Louis, Mo.) was used as model antigen.

Groups of five mice were injected subcutaneously with 50 µg of OVA alone in PBS or mixed with *P. senega* or Quil A saponins in 100 µl of PBS. Mice were immunized twice using the immunization protocol shown in Table 2.

TABLE 2

| | | Immunization Protocol | | | |
|---|---|---|---|---|---|
| Group | Saponin | OVA | 0 | 14 | 28 |
| Control | None | 50 µg | 1 | 1,2 | 1,2,3 |
| Quil A | 50 µg | 50 µg | 1 | 1,2 | 1,2,3 |

TABLE 2-continued

| | | Immunization Protocol | | | |
|---|---|---|---|---|---|
| Group | Saponin | OVA | 0 | 14 | 28 |
| *P. senega* | 200 µg | 50 µg | 1 Vaccination | 1,2 Bleed Boost | 1,2,3 Bleed Spleen cells |

5 mice/group
[1]Subcutaneous immunization.
[2]Bleeding (serum IgG anti-OVA).
[3]Spleen cells (OVA specific IL-2).

Sera were prepared from blood obtained at 10 or 14 and 20 or 28 days after the primary inoculation. All sera were clarified by centrifugation and stored at −20° C. until analysis by ELISA. At days 20 or 28, the mice were euthanized and the spleens were removed. Spleen cells were prepared by grinding the tissues through 70 µm cell strainer (Falcon, Becton Dickinson Labware, Franklin Lakes, N.J.) and rinsing with RPMI-1640 containing 10% fetal bovine serum (GibcoBRL, Life Technologies Inc., N.Y.) (RPMI-FCS). Spleen cells were centrifuged at 300 g at 4° C. for 5 min, the supernatant discarded, and the cell pellet treated with 1 ml of a 1% ammonium chloride solution. The cells were washed by centrifugation twice, suspended in RPMI-FCS, counted and adjusted to a cell concentration of $10^7$ cells/ml.

ELISAs were used to measure serum IgG, $IgG_{2a}$ and $IgG_1$ anti-OVA. The wells of 96-well microtiter plates (Immulon 2; Dynatec, Laboratories Inc., Chantilly, Va.) were coated with 10 µg/ml of OVA in PBS at 4° C. for 18 h. The wells of all plates were washed three times with PBS containing 0.05% Tween-20 (PBS-T) and incubated with PBS containing 1% bovine serum albumin (BSA) at 37° C. for 30 min, plates were then washed with PBS-T. To the plates, 100 ml of 1:100 mouse serum dilutions for IgG anti-OVA or 1:10 for $IgG_{2a}$ and $IgG_1$ in PBS-T were added and incubated at 37° C. for 1 h. After washing with PBS-T, biotinylated goat anti-mouse IgG, $IgG_{2a}$ or $IgG_1$ (Southern Biotechnology Associates, Birmingham, Ala.) diluted 1:1000 in PBS-T were added and incubated at 37° C. for 1 h. After washing with PBS-T, 100 ml of streptavidin-alkaline phosphatase conjugate (Gibco BRL, Life Technologies Inc., Gaithersburg, Md.) was added and incubated at 37° C. for 1 h. The plates were washed with PBS-T and 100 ml of the alkaline phosphatase substrate solution added to each well. The substrate consisted of 1 mg/ml of p-nitrophenyl phosphate (104 phosphatase substrate tablets; Sigma) in 1 M diethanolamine buffer, pH 9.8. The absorbance of each well at 405 nm was measured using an automated spectrophotometer (Molecular Devices $V_{max}$ Kinetic microplate reader; Molecular Devices, Menlo Park, Calif.). Immunoglobulin levels were reported as the optical density (OD) readings, after the subtraction of the OD read-out of the mean plus 3 standard errors of the mean (SEM) of a series of control wells with normal mouse serum added, and expressed as means±SEM or ±SDM for each group, and compared by the analysis of variance (ANOVA) Tukey test.

Figure 5:
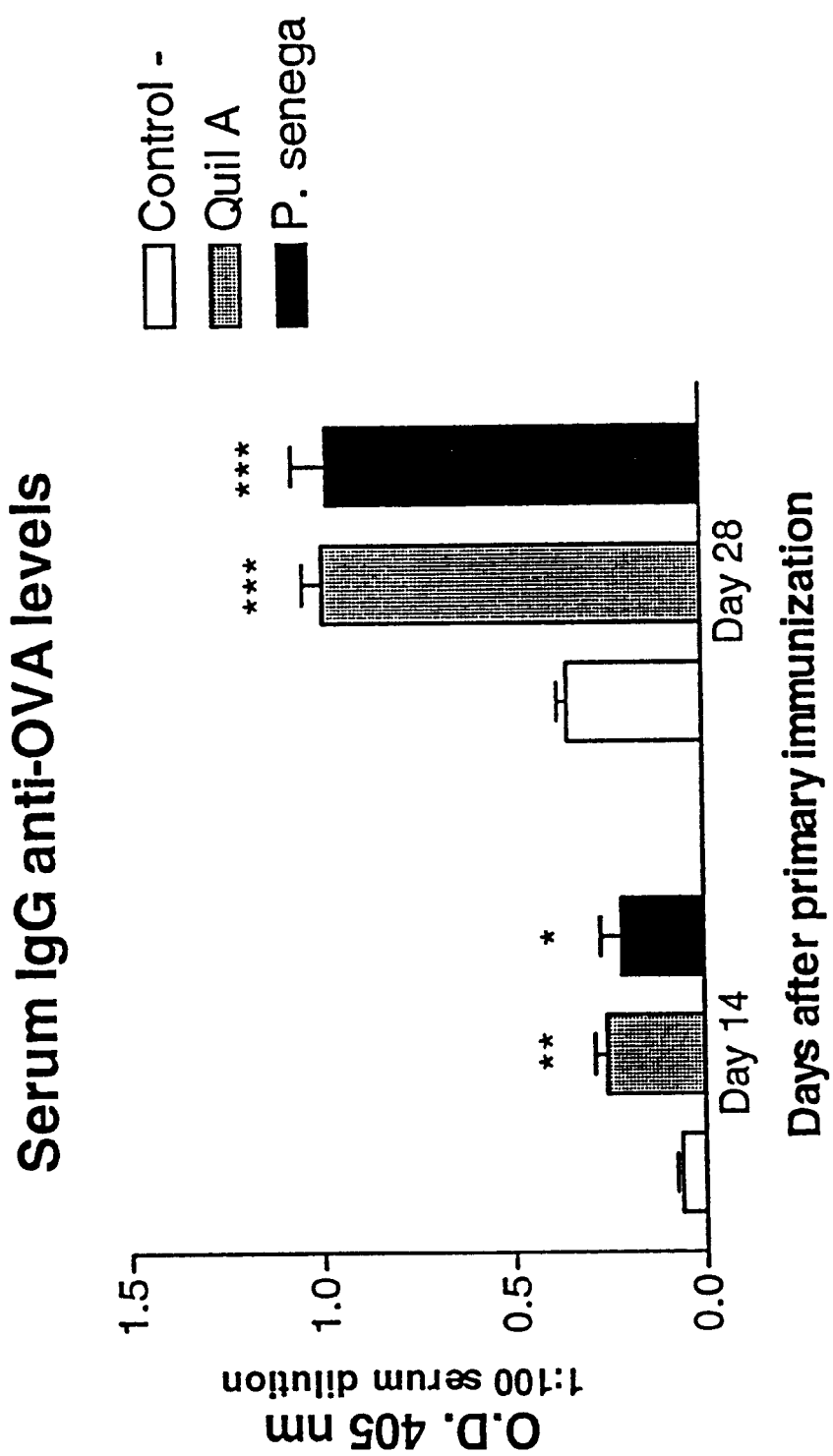
FIG. 5 depicts the serum IgG responses to ovalbumin immunization (at days 0, 14 and 28) co-administered with *P. senega* saponins or Quil A saponins.

FIG. 5 shows the time response of serum IgG anti-ovalbumin responses following immunization at days 0 and 14 with 50 µg of ovalbumin co-administered with *P. senega* saponins or Quil A saponins. The control group was immunized with ovalbumin in saline. IgG anti-ovalbumin levels were determined, at days 14 and 28 post-immunization, by ELISA. The bars represent the mean values of groups of five mice±SE. Asterisks signify statistical significance as follows: *$P<0.05$, $P<0.01$, *$P<0.001$ versus control group.

As can be seen in FIG. 5, the primary immune response, measured on day 14, was higher for the groups which had been administered both, Quil A and *P. senega* saponin adjuvants. The secondary immune response, measured on day 28, indicated that IgG responses were equivalent in magnitude for both the Quil A and *P. senega* saponin adjuvants.

To measure antigen-Specific IL-2, IL-4 and IFN-γ cytokine responses, splenic lymphocytes in RPMI-FCS were added in 100 μl volumes containing $10^7$ cells/ml to each of the wells of 96-well round-bottom cell culture microtiter plates (Corning Glass Works, Corning, N.Y.). To stimulate the cells, 100 μg of OVA in 100 μl of RPMI-FCS were added to each well in triplicate cultures. Cells cultured in growth medium only were used as negative controls. The plates were placed at 37° C. in an atmosphere containing 5% $CO_2$ for 72 h. The spleen culture supernatants were collected and tested for IL-2, IL-4 and IFN-γ cytokines by ELISA. The wells of 96-well microtiter plates were coated with 5 μg of anti-IL-2, IL-4 and IFN-γ cytokines monoclonal antibodies (PharMingen, San Diego, Calif.) in 50 μl of PBS at 4° C. for 18 h. The plates were washed with PBS-T and dilutions of culture supernatants from 1:2 to 1:128 in PBS-T were added to the wells and incubated at 37° C. for 2 h. After washing with PBS-T, 50 μl of biotinylated anti-IL-2, IL-4 and IFN-γ monoclonal antibodies (PharMingen) diluted 1:1000 in PBS-T were added to the wells and incubated at 37° C. for 2 h. The plates were washed with PBS-T and 50 μl of streptavidin-alkaline phosphate conjugate, diluted 1:1000 in PBS-T, were added to the wells and incubated at 37° C. for 1 h. The plates were washed with PBS-T and 100 μl of the alkaline phosphatase substrate solution added to each well. The absorbance of each well at 405 nm was measured in an automated spectrophotometer. The culture supernatant samples were analysed individually. The IL-2, IL-4 and IFN-γ amounts were calculated by standard curves using recombinant murine IL-2, IL-4 and IFN-γ. Data were expressed as the amount of IL-2 in culture supernatants in pg/ml for IL-2 and IL-4 cytokines and ng/ml for IFN-γ, and expressed as means±SEM or ±SDM for each group (5 mice).

Figure 6:
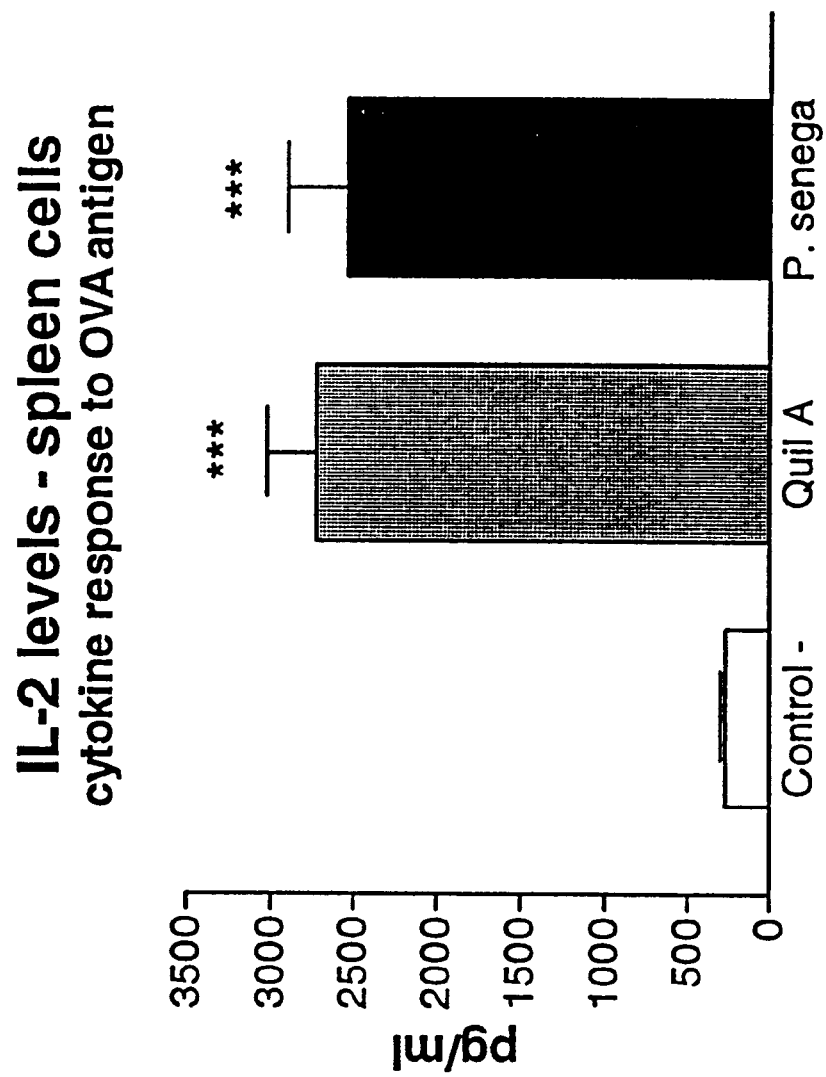
FIG. 6 depicts the effect of saponins on IL-2 release in spleen cells culture supernatant.

FIG. 6 shows the release of IL-2 in spleen cell culture supernatants. Spleen cells ($10^6$ cells/well) were co-cultured with ovalbumin (OVA) (10 μg/well) for 72 h. The supernatants were harvested and tested for the amount of IL-2 released by ELISA. The IL-2 amounts were calculated by a standard curve using recombinant murine IL-2. The data are expressed as the amount of IL-2 in culture supernatants in pg/ml. The bars represent the mean values of groups of five mice±SE. Three asterisks signify statistical significance of $P<0.001$ versus control group.

These results demonstrate that the administration of Quil A and *P. senega* saponins to mice primed the specific cellular immune responses to OVA. When spleen cells of the immunized mice were cultured in vitro in the presence of the antigen OVA, the cells induced the production of IL-2 in an equivalent magnitude for both the Quil A and *P. senega* saponin groups.

EXAMPLE 3

Stimulation of Anti-IgG Response to Subcutaneous Administration of *P. Senega*

In order to confirm that the *P. senega* saponin adjuvant compositions were indeed able to stimulate an anti-IgG response when administered subcutaneously, an additional experiment was carried out in mice. In particular, OVA was used to immunize mice by the subcutaneous route. Mice were immunized on days 0 and 10 with 50 μg of OVA or OVA formulated with the Quil A and *P. senega* saponins, as shown in Table 3. Serum samples were obtained from the animals on days 10 and 20 and anti-OVA IgG, $IgG_1$ and $IgG_{2a}$ measured by ELISA.

TABLE 3

| | | | Immunization Protocol | | |
|---|---|---|---|---|---|
| Group | Saponin | OVA | 0 | 10 | 20 |
| Control | None | 50 μg | 1 | 1,2 | 1,2,3,4 |
| Quil A | 50 μg | 50 μg | 1 | 1,2 | 1,2,3,4 |
| *P. senega*-1 | 50 μg | 50 μg | 1 | 1,2 | 1,2,3,4 |
| *P. senega*-1 | 200 μg | 50 μg | | | |
| *P. senega*-2 | 50 μg | 50 μg | | | |
| *P. senega*-2 | 200 μg | 50 μg | | | |
| | | | Vaccination | Bleed Boost | Bleed Spleen cells |

5 mice/group
[1] Subcutaneous immunization.
[2] Bleeding (serum IgG anti-OVA).
[3] Bleeding (serum IgG, $IgG_{2a}$ and $IgG_1$ anti-OVA).
[4] Spleen cells (OVA specific IL-2, IFN-γ and IL-4).

Figure 7:
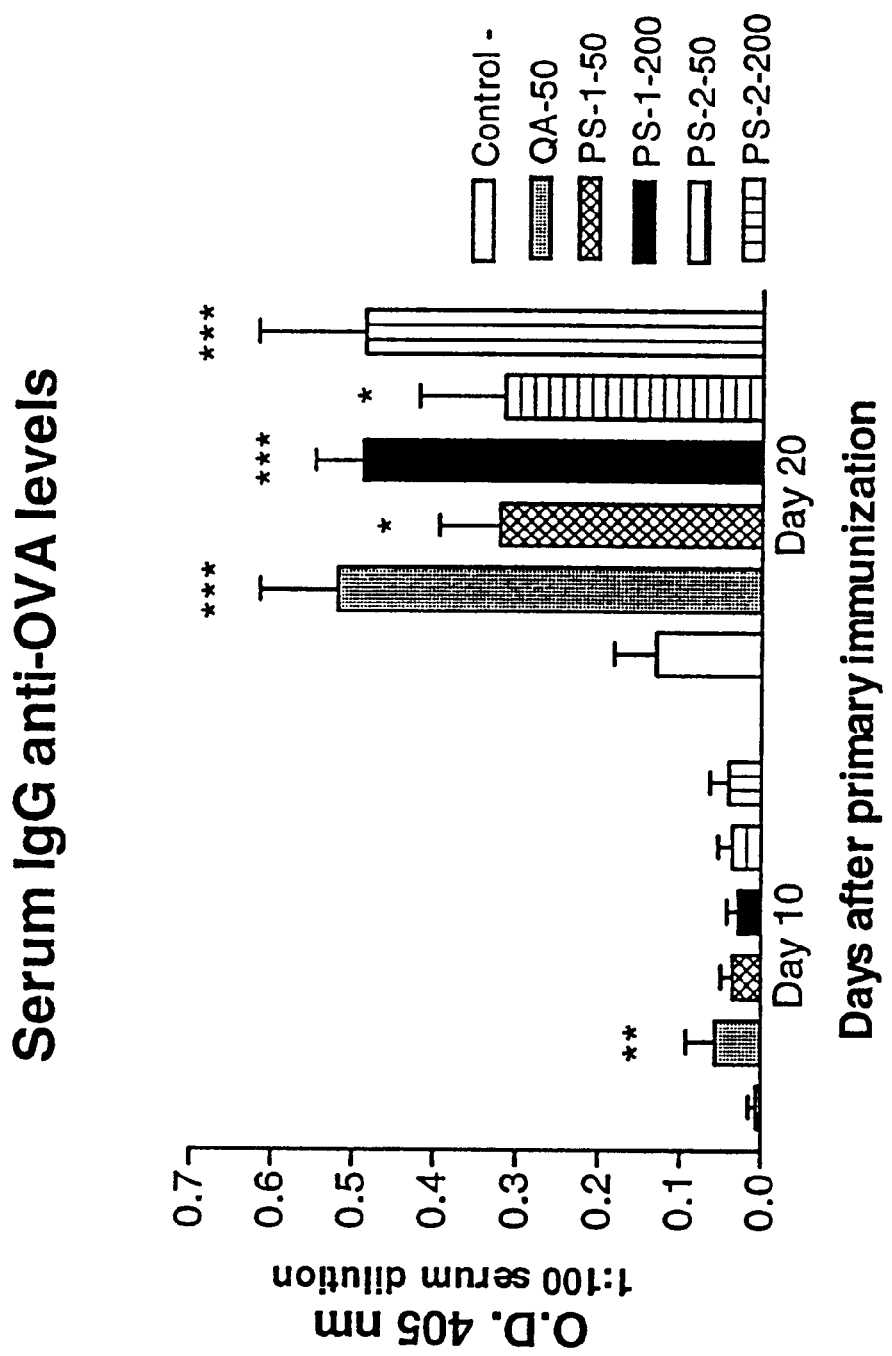
FIG. 7 depicts serum IgG responses to ovalbumin immunization (at days 0, 10 and 20) co-administered with *P. senega* saponins or Quil A saponins.

FIG. 7 shows the time response of serum IgG anti-ovalbumin responses following immunization at days 0 and 10 with 50 μg of ovalbumin co-administered with *P. senega* saponins (fractions 1 and 2) or Quil A saponins. The control group was immunized with ovalbumin in saline. IgG anti-ovalbumin levels were determined at days 10 and 20 post-immunization, by ELISA. The bars represent the mean values of groups of five mice±SD. Asterisks signify statistical significance as: *$P<0.05$, $P<0.01$, *$P<0.001$ versus control group.

As can be seen, animals that received the vaccine containing the Quil A and *P. senega* saponins showed significantly higher IgG antibody levels than animals that received OVA without the saponins at day 20 after primary immunization.

Figure 8:
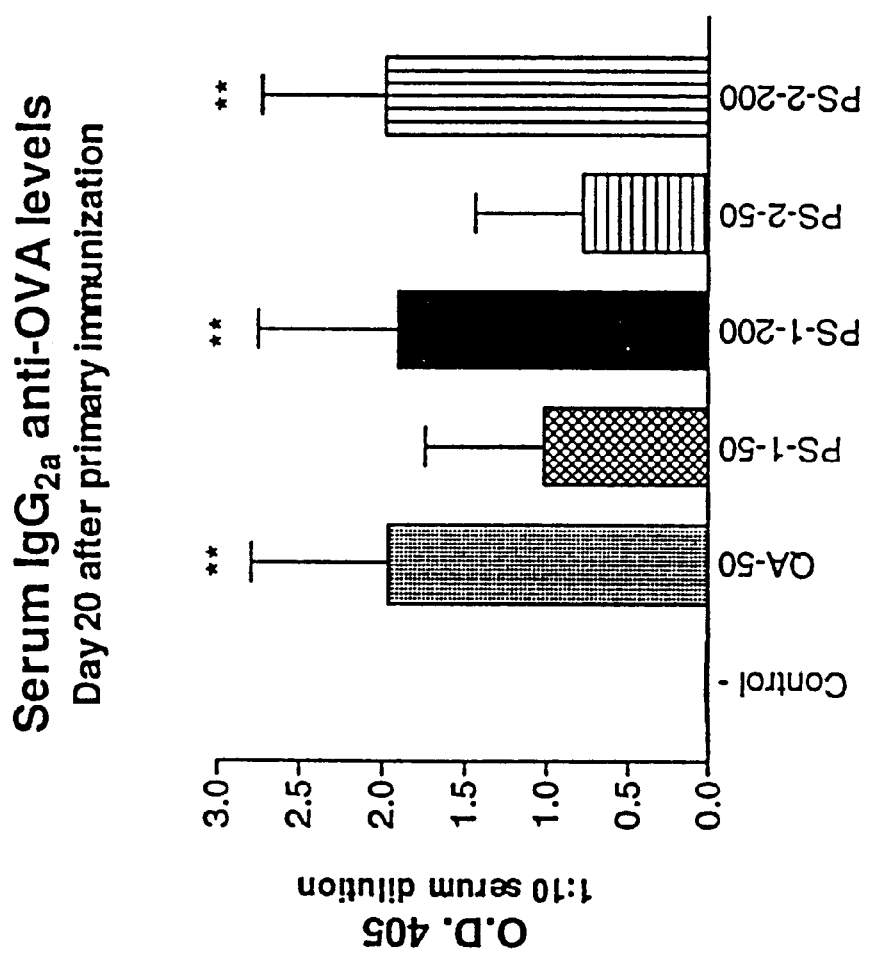
FIG. 8 depicts serum $IgG_{2a}$ anti-ovalbumin responses following immunization at day 0 with 50 μg of ovalbumin co-administered with *P. senega* saponins or Quil A saponins.

FIG. 8 shows serum $IgG_{2a}$ anti-ovalbumin responses following immunization at days 0 and 10 with 50 μg of ovalbumin co-administered with *P. senega* saponins (fractions 1 and 2) or Quil A saponins. The control group was immunized with ovalbumin in saline. $IgG_{2a}$ anti-ovalbumin levels were determined at day 20 post-immunization, by ELISA. The bars represent the mean values of groups of five mice±SD. Asterisks indicate statistical significance of $P<0.01$ versus control group.

Figure 9:
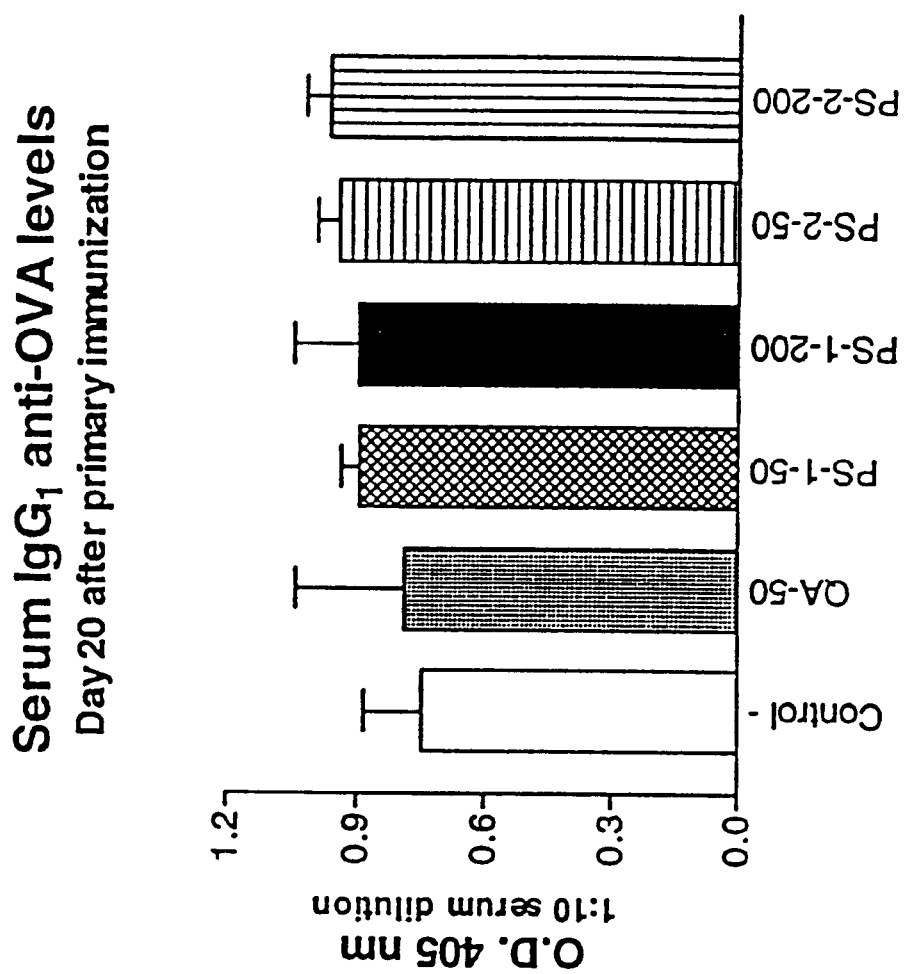
FIG. 9 depicts serum $IgG_1$ anti-ovalbumin responses following immunization at day 10 with 50 μg of ovalbumin co-administered with *P. senega* saponins or Quil A saponins.

FIG. 9 shows serum $IgG_1$ anti-ovalbumin responses following immunization at days 0 and 10 with 50 μg of ovalbumin co-administered with *P. senega* saponins (fractions 1 and 2) or Quil A saponins. The control group was immunized with ovalbumin in saline. $IgG_1$ anti-ovalbumin levels were determined, at day 20 post-immunization, by ELISA. The bars represent the mean values of groups of five mice±SD.

As shown in FIGS. 8 and 9, serum $IgG_{2a}$ at day 20 following primary immunization were significantly enhanced with Quil A and with the higher *P. senega* saponin doses compared to the control mice; $IgG_1$ levels showed no differences among groups.

Figure 10:
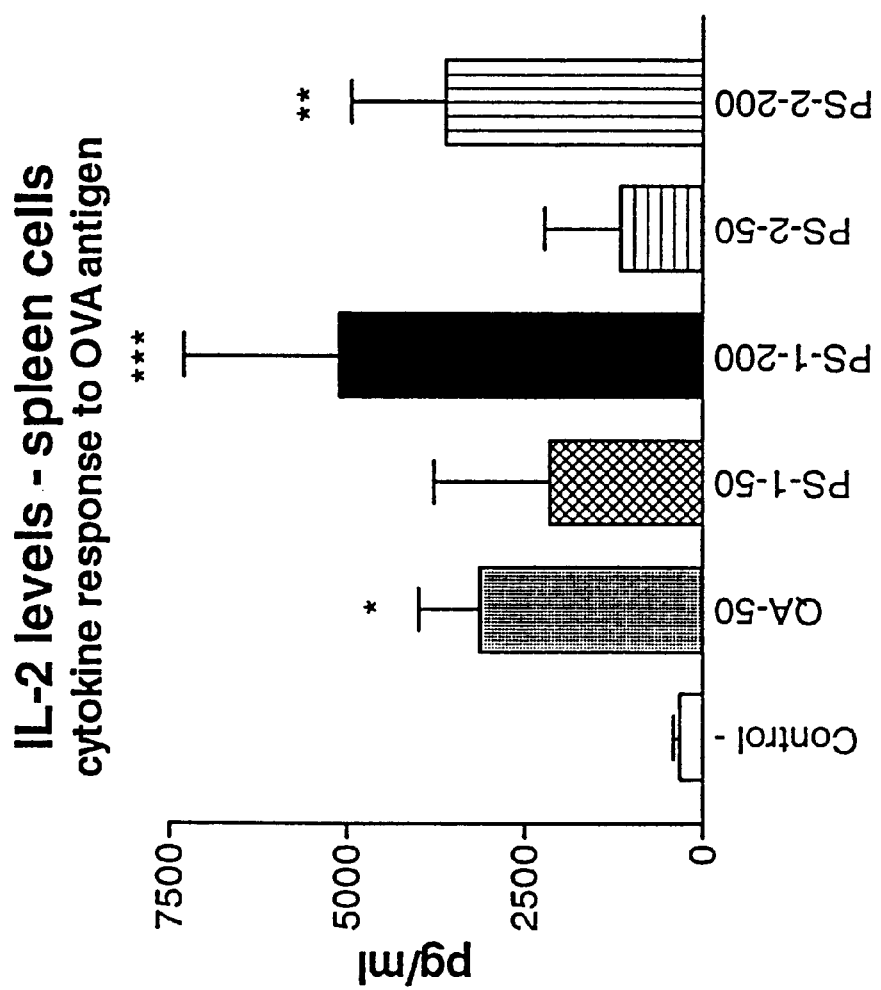
FIG. 10 depicts the effect of saponins on the release of IL-2 in spleen cells culture supernatants.

FIG. 10 shows release of IL-2 in spleen cells culture supernatants. Spleen cells ($10^6$ cells/well) were co-cultured with ovalbumin (OVA) (10 μg/well) for 72 h. The supernatants were harvested and tested for the amount of IL-2 released by ELISA. The IL-2 amounts were calculated by a standard curve using recombinant murine IL-2. The data are expressed as the amount of IL-2 in culture supernatants in pg/ml. The bars represent the mean values of groups of five mice±SD. Statistical significance is shown by asterisks as follows: *P<0.05, P<0.01, *P<0.001 versus control group.

Figure 11:
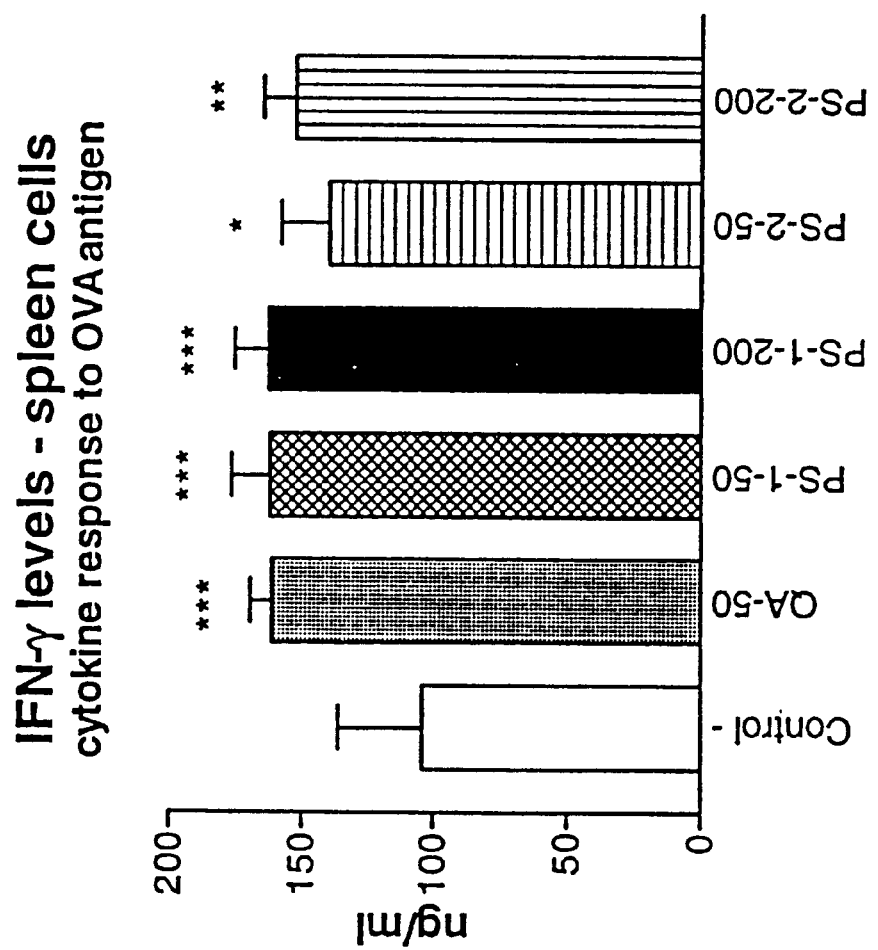
FIG. 11 depicts the release of IFN-γ cytokines in spleen cells culture supernatants.

FIG. 11 shows the release of IFN-γ cytokine in spleen cells culture supernatants. Spleen cells ($10^6$ cells/well) were co-cultured with ovalbumin (OVA) (10 μg/well) for 72 h. The supernatants were harvested and tested for the amount of IFN-γ released by ELISA. The IFN-γ amounts were calculated by standard curves using recombinant murine IFN-γ. The data are expressed as the amount of IFN-γ in culture supernatants in ng/ml and pg/ml, respectively. The bars represent the mean values of groups of five mice±SD. Asterisks indicate statistical significance as follows: *P<0.05, P <0.01, *P<0.001 versus control group.

Figure 12:
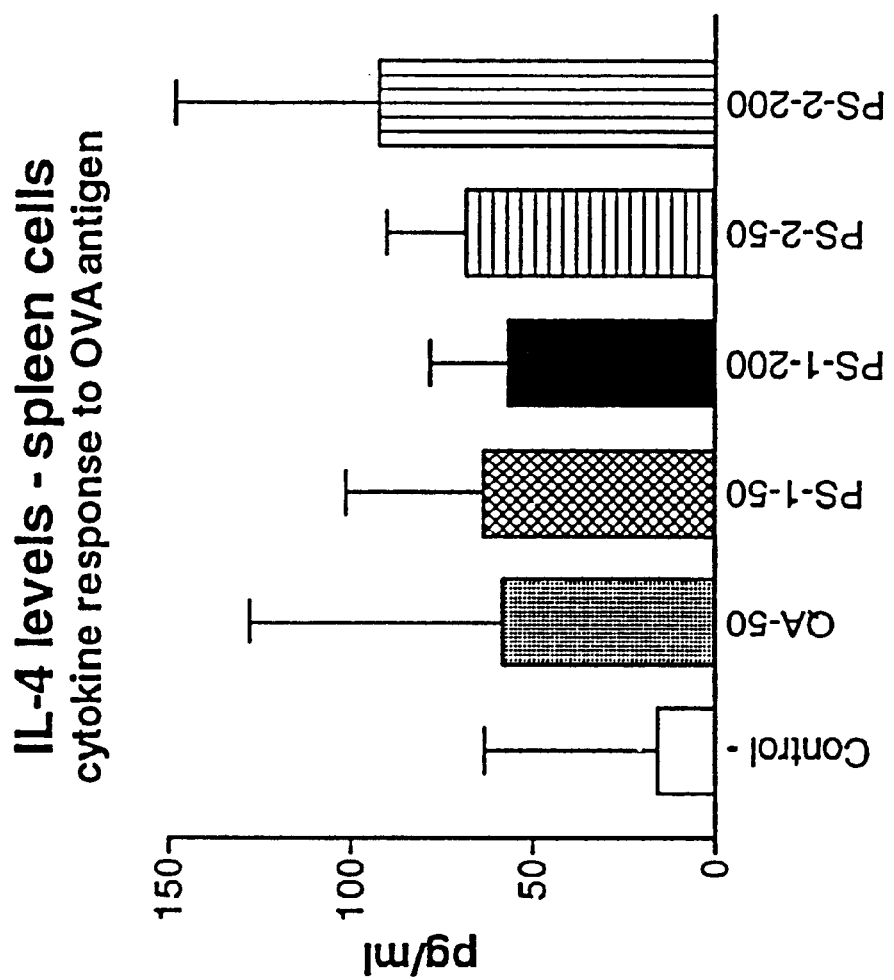
FIG. 12 depicts the release of IL-4 cytokines in spleen cells culture supernatants.

FIG. 12 shows the release of IL-4 cytokine in spleen cells culture supernatants. Spleen cells ($10^6$ cells/well) were co-cultured with ovalbumin (OVA) (10 μg/well) for 72 h. The supernatants were harvested and tested for the amount of IL-4 released by ELISA. The IL-4 amounts were calculated by standard curves using recombinant murine IL-4. The data are expressed as the amount of IL-4 in culture supernatants in ng/ml and pg/ml, respectively. The bars represent the mean values of groups of five mice±SD. Asterisks indicate statistical significance as follows: *P<0.05, P<0.01, *P<0.001 versus control group.

As can be seen, FIGS. 10, 11 and 12 indicate that the administration of Quil A and P. senega saponins to mice primed specific cellular immune responses, significantly augmenting the in vitro production of IL-2 and IFN-γ cytokines by spleen cells in response to OVA antigen. No saponin effect was observed on the induction of IL-4 cytokine. The effect of Quil A and P. senega. saponins on the levels of $IgG_{2a}$ and $IgG_1$ immunoglobulins and IFN-γ and IL-4 cytokines appears to be consistent with the induction of a $Th_1$ type cellular immune response.

EXAMPLE 4

Enhanced Immune Response in Poultry with Co-administration of P. Segena Saponins This example shows the effect of P. segena saponins on the immune response in poultry. Isobrown laying hens from the Poultry Research Unit of the University of Saskatchewan (Saskatoon, Canada) were used in the experiment. The birds were housed in individual cages. Groups of ten hens were injected intramuscularly in the breast muscle with 1 ml of rotavirus antigen mixed with Quil A or P. senega saponins. The hens were immunized three times as the protocol below indicates.

TABLE 4

| Group | Saponin | Rotavirus | Immunization Protocol | | | | | |
|---|---|---|---|---|---|---|---|---|
| | | | 0 | 14 | 28 | 42 | 56 | 70 |
| Control | None | 0.5 ml | 1 | 1 | 1,2 | 2 | 2 | 2 |
| Quil A | 0.3 mg | 0.5 ml | 1 | 1 | 1,2 | 2 | 2 | 2 |
| P. senega-1 | 1 mg | 0.5 ml | 1 | 1 | 1,2 | 2 | 2 | 2 |
| P. senega-1 | 1 mg | 0.5 ml | 1 | 1 | 1,2 | 2 | 2 | 2 |

10 hens/group
[1]Intramuscular immunization.
[2]Egg collection (egg IgG anti-rotavirus).

Eggs were collected on day 28 before immunization and on days 42, 56 and 70 of the experiment for the analysis of egg IgG anti-rotavirus antibodies. The eggs were cracked and the whites and yolks were homogenized using a polytron. 100 μl of the homogenized egg was then mixed with 500 μl of citrate-phosphate buffer pH 5.0 in a 96 deep-well sample block and stored at −20° C. until analysis by ELISA at the end of the experiment.

Anti-rotavirus IgG levels in the egg samples were analyzed by ELISA as follows. All samples were thawed and diluted to 1:600 using citrate-phosphate buffer pH 5.0. The samples were then centrifuged at 3000×g for 15 minutes to remove the fat and precipitated proteins. The wells of 96 well microtiter plates were filled with 50 μl of a 1:100 dilution of the rotavirus antigen used for vaccine preparation and incubated at 4° C. for 18 h. The wells of all plates were washed three times with PBS-T and incubated with PBS containing 1% BSA at 37° C. for 30 min. The plates were washed with PBS-T and 50 μl of the egg samples were then added into duplicate wells of the microtiter plates and incubated at 37° C. for 2 h. The plates were washed with PBS-T and 50 μl of a 1:10,000 dilution of goat anti-chicken horseradish peroxidase conjugate were added to the wells. After incubation at 37° C. for 1 h, the plates were washed with PBS-T and 50 μl of tetramethylbenzidine (TMB) substrate were added to the wells and incubated at room temperature for 20 min. The absorbance of the wells at 650 nm was measured using an automated spectrophotometer. Two absorbances were averaged and the mean absorbance of control normal egg, non-immunized samples was subtracted. Results were expressed as means±SDM and compared by the analysis of variance (ANOVA) Tukey test.

Figure 13:
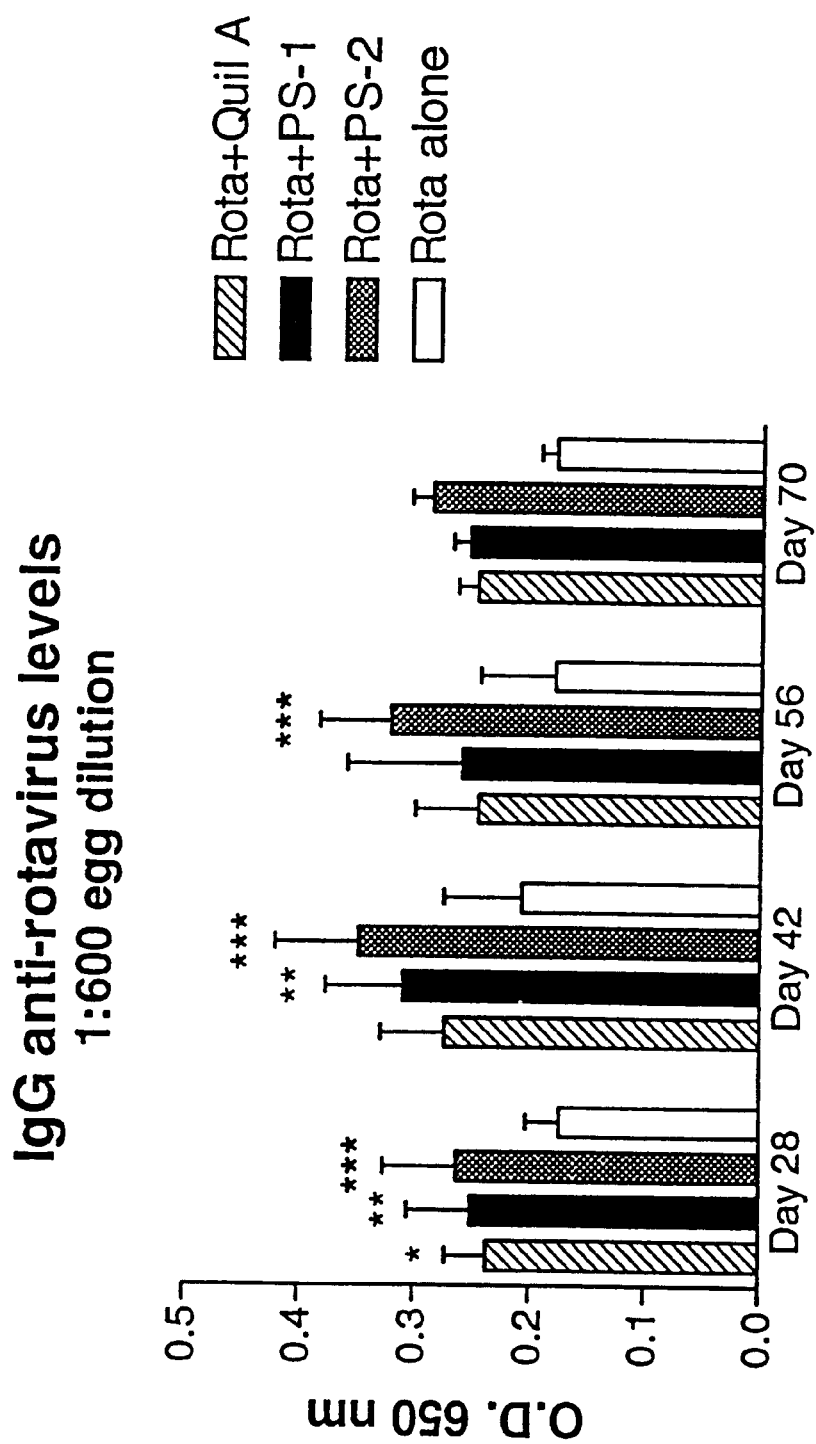
FIG. 13 depicts the time response of egg-yolk IgG antirotavirus responses following immunization with rotavirus co-administered with *P. senega* saponins or Quil A saponins.

FIG. 13 shows the time response of egg-yolk IgG anti-rotavirus responses following immunization at days 0, 14 and 28 with rotavirus co-administered with P. senega saponins or Quil A saponins. The control group was immunized with rotavirus alone. IgG anti-rotavirus levels were determined at days 28, 42, 56 and 70 post-immunization, by ELISA. The bars represent the mean values of groups of ten hens±SD. Asterisks indicate statistical significance as follows: *P<0.05, P<0.01, *P<0.001 versus control group.

As shown in FIG. 13, Quil A and P. senega fractions 1 and 2 consistently increased the response to rotavirus compared to the birds that were given no saponin. P. senega fraction 2 induced the highest responses which were significantly higher compared to the control group on days 28, 42 and 56. Anti-rotavirus responses peaked on day 42 and declined by day 56.

EXAMPLE 5

Further Purification and Characterization of P. Senega Saponins

A. Fractionation of P. Senega Extracts by Flash Chromatography Using Isocratic Elution.

To further characterize P. senega saponins useful in the formulation of adjuvant compositions, saponins were extracted from the roots of P. senega L. essentially as described in Example 1. P. senega saponins were extracted from roots using 100% methanol (MeOH) and a Soxhlet apparatus. Dry roots from P. senega L. were ground into a fine powder, defatted in hexane and extracted with MeOH. A brown syrup-like, crude extract was obtained upon evaporation of MeOH and was freeze-dried.

The crude extract was suspended in water and centrifuged (Beckman J2-21M/E; 10,000 rpm, 15 min) to remove any undissolved substances. The supernatant was filtered (Whatman f.p. 202 grade) and extracted with n-butanol (n-BuOH) saturated with water. The upper butanolic layer, containing saponins, was evaporated under vacuum to give a crude butanolic extract (2.5%).

Open column chromatography (flash chromatography) was used to further purify the crude extract. The column (60 cm-length; 25 mm-internal diameter) was packed with a slurry of silica gel (10–40 µm, type H, Sigma, St. Louis, Mo.) in chloroform ($CHCl_3$)/methanol (MeOH)/water ($H_2O$); 65/35/10, lower phase). The dried butanolic extract was dissolved in a minimal amount (approximately 1 ml) of chloroform ($CHCl_3$)/methanol (MeOH)/water ($H_2O$); 65/35/10, lower phase) and applied with a pipette to the top of the silica gel.

The column was subsequently eluted under isocratic conditions using ($CHCl_3$)/methanol (MeOH)/water ($H_2O$); 65/35/10 lower phase). A total of 25 fractions were collected consisting of 10 ml each.

All eluted fractions were analyzed by thin layer chromatography (TLC) using n-butanol:acetic acid:water (40:10:50; upper phase) (Wagner et al., *Plant Drug Analysis: A Thin Layer Chromatography Atlas*, pp. 225–245. Springer-Verlag, New York). The developed plates were air-dried, observed under UV light and sprayed with the anisaldehyde-sulphuric acid reagent (ASR) (Wagner et al., supra). Bands were visualized after color development upon heating. Fractions 4–21 were identified as containing a mixture of purified saponins.

Because saponins are known to lyse red blood cells, the hemolytic activity of these fractions was tested. The assay for hemolytic activity was performed essentially as described in Example 1. One mg of the saponins in PBS were added to the top wells and double dilutions were performed. The saponin content was estimated as the last dilution presenting complete hemolysis of the red cells and expressed as hemolytic units (HU) per mg of material. The hemolytic activity of *P. Senega* fraction 5 was 128 HU per mg.

B. Further Spectroscopic Analysis of Fraction 5.

Based on its hemolytic activity, further spectroscopic analysis was carried out on Fraction 5. HPLC analysis was carried out essentially as described in Example 1. Briefly, analyses were performed on a Waters Nova-Pak® 60 Å 4 µm (15 cm×3.9 mm, i.d.) $C_{18}$ column. The chromatographic run was carried out under isocratic conditions using the following solvent system: 25% solution A [10% ammonium acetate buffer ($CH_3COONH_4$; pH 6.9, 50 mm)—90% acetonitrile ($CH_3CN$)], and 75% solution B [90% ammonium acetate buffer (pH 6.9, 50 mm)—10% acetonitrile]. The fraction was dissolved in solution B and filtered before it was injected into the column. The injection volume was 20 µl and the mobile phase flow rate was 1 ml/min. The column effluent was monitored at 315 nm. The HPLC profile of Fraction 5 showed a dominant peak with a retention time of 2.9 minutes, indicating a purity of approximately 80% based on peak area percent.

UV spectra was also taken of Fraction 5. The HPLC instrument used for the analysis was equipped with a photodiode array detection system (Waters 996 Photodiode Array Detector; Waters, Milford, Mass.). The detection system was programmed to scan between 200 and 350 nm in the UV range. Samples were suspended in 25% solution A/75% solution B. Detection of the column effluent in the range of 200 to 350 nm produced two absoption maxima at λ 328.0 and 233.5 nm. The maximum at 328.0 nm is due to a chromophore present in one of the side chains of the saponin compound shown in FIG. 14, named 3,4-dimethoxycinnamic acid. The maximum at 233.5 nm is due to the triterpenoid aglycone present in the saponin compound.

NMR data on Fraction 5 was obtained using an $^1$H-NMR Bruker AM-300 spectrometer. Samples were dissolved in deuterated methanol. The NMR results can be described relative to the exemplary saponin shown in FIG. 14. The signal at 5.85 ppm corresponds to proton from the methyl groups present in the aglycone and signals in the region 3.70–4.00 ppm correspond to the methoxy (–$OCH_3$) group of the 3,4-dimethoxycinnamic acid chromophore present in the sugar side chain. Furthermore, the signals at 6.00 and 7.00 ppm are due to the double bond present in the chromophore, and the signals in the region of 7.2 to 8.20 ppm are due to the protons from the benzyl group present in the 3,4-Dimethoxycinnamic acid.

Mass spectra was obtained for Fraction 5 by Fast Atom Bombardment (FAB) using Fisions 70SE mass spectrometer operating in the negative mode with a cesium (Cs) source. Samples were suspended in glycerol, which served as the matrix. The mass spectrum in the negative mode revealed a strong molecular ion at m/z 1455.8 $(M-H)^-$. The ion at m/z 1455 $(M-H)^-$ corresponded to a senegin II saponin isolated from *P. senega* L. var. *latifolia* Torry et Gray (Shoji et al., *Chem. Pharm. Bull.* (1973) 21:791–799; Tsukitani and Shoji, *Chem. Pharm. Bull.* (1973) 21:1564–1574; Yoshikawa et al., *Chem. Pharm. Bull.* (1995) 43:350–352).

Electrospray liquid chromatography (LC)/mass spectroscopy (MS) analysis was performed for fraction 5 using a Micromass Quattro LC instrument (Micromass, Manchester, Great Britain), with a scan range of 600 to 1600 mass/charge (m/z) and a scan time of 3.3 seconds. The LC analysis was performed under isocratic conditions: 25% solution A-75% solution B. The step solutions were as follows: solution A, 10% ammonium acetate buffer (5 mM, pH 5.7), 90% acetonitrile; and, Solution B, 90% ammonium acetate buffer (5 mM, pH 5.7), 10% acetonitrile. The flow rate was 0.350 ml/minute, and the injection volume was 2 µl. Analysis time was 30 minutes. This analysis showed the presence of a molecular ion at 1455.9 m/z., as well as, fragment ions resulting from the cleavage of sugar moieties that are present in saponin.

Figure 14:
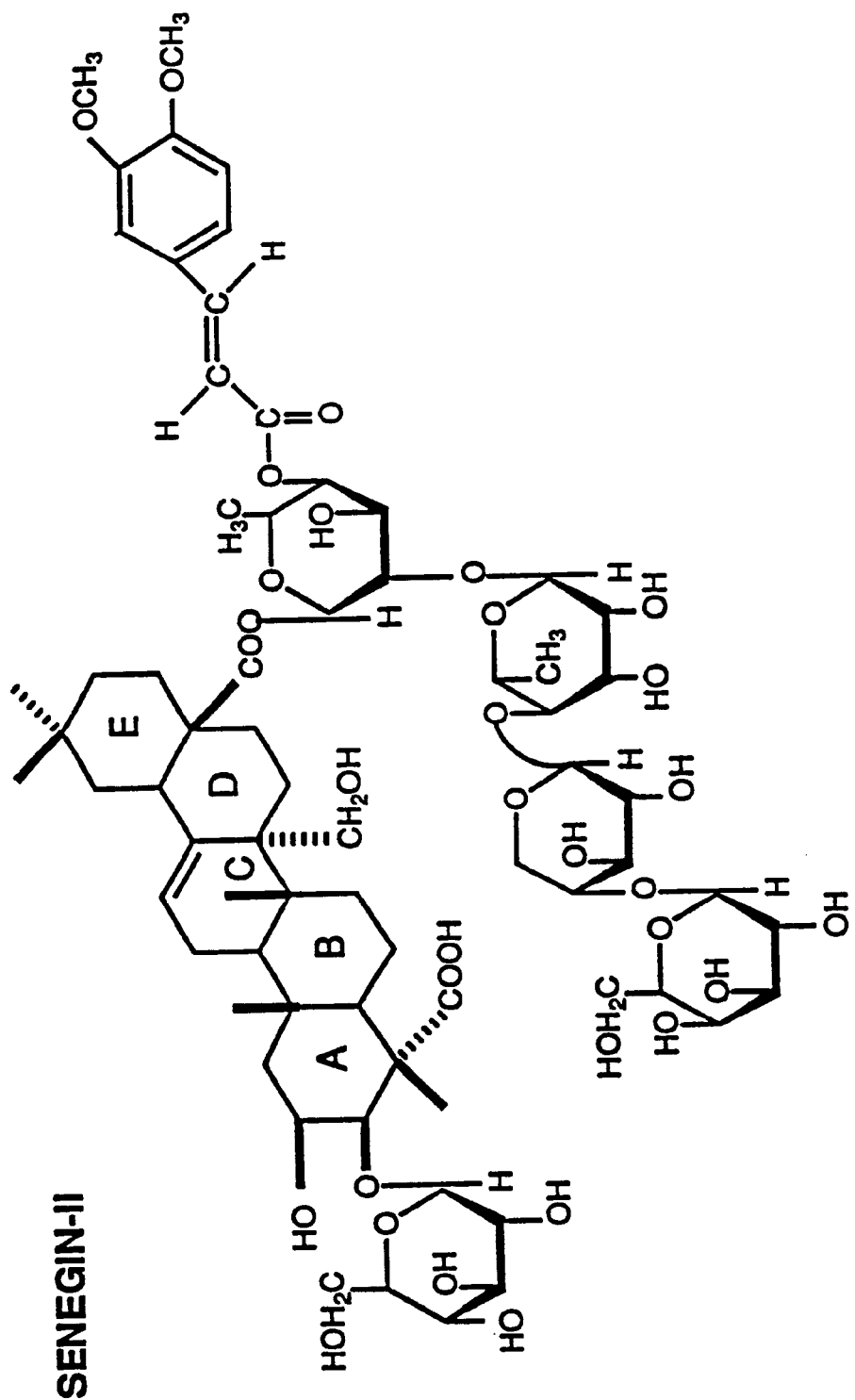
FIG. 14 depicts a *P. senega* saponin (senegin II) useful in the practice of the present invention.

Comparison of the above-described experimental data with saponin spectroscopic data available in the literature (for example, Tsukitani, et al., supra) suggests that Fraction 5 contains a saponin in the senegin II family (FIG. 14).

Fraction 5 was used for further immunological studies (below).

EXAMPLE 6

Adjuvant Activity of a Pure (Fraction 5) *P. Seneca* Saponin

To examine the activity of a pure (Fraction 5, described in Example 5) *P. senega* saponin, the following experiment was carried out in mice. Two groups of four mice were used. The first group was subcutaneously injected with 50 µg of ovalbumin (OVA) alone in 100 µl of PBS. The second group was injected with 50 µg of ovalbumin (OVA) mixed with 50 µg of Fraction 5 saponin in 100 µl of phosphate buffered saline (PBS). All mice were immunized twice, once at day zero and once at day ten. The mice were bled 10 days after the last immunization (at day 20).

Figure 15:
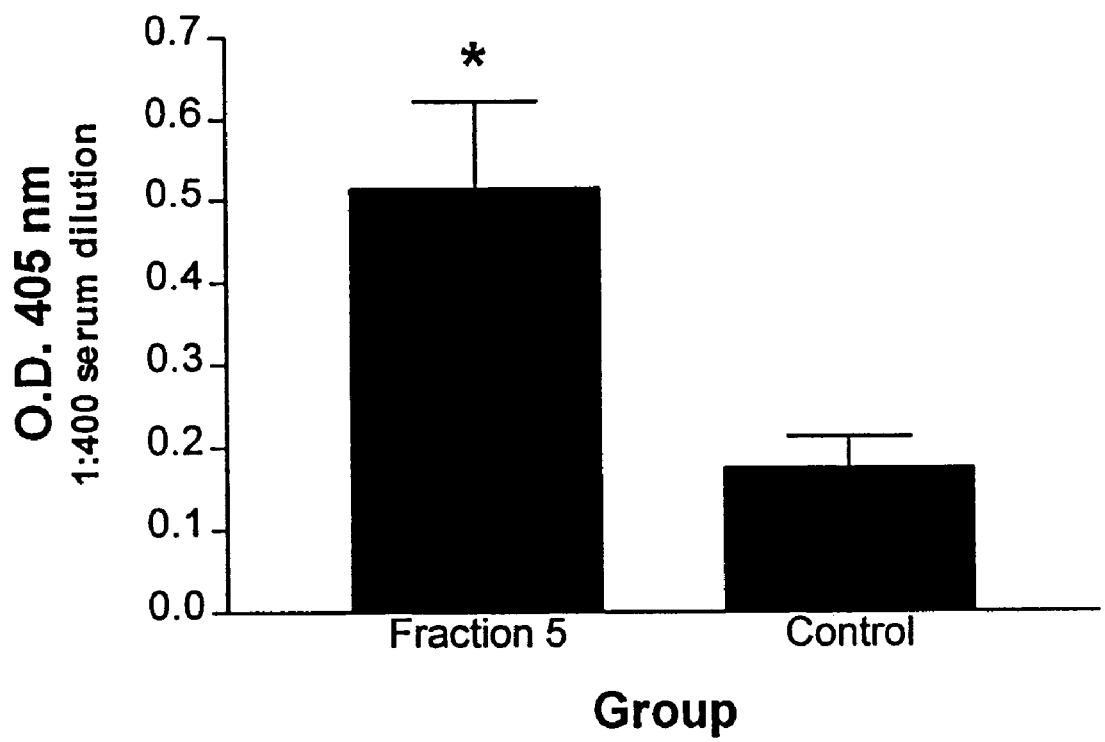
FIG. 15 depicts serum IgG anti-ovalbumin responses following immunization at days 0 and 10 with 50 μg of ovalbumin co-administered with *P. senega* saponin, fraction 5.

FIG. 15 shows the serum IgG anti-ovalbumin serum responses following the immunizations. IgG anti-ovalbumin levels were determined at day 20 by ELISA. In FIG. 15, the bars represent the mean values of the groups of four mice±SEM (standard error of the mean).

The asterisk signifies statistical significance: *P<0.05, versus the control group.

These results indicate that the purified Fraction 5 *P. senega* saponin demonstrates significant immunological activity as an adjuvant. Evaluation of specific cellular immune response is carried out as essentially as described in Example 3.

Thus, novel *P. senega* saponin compositions and methods for using the same are disclosed. Although preferred embodiments of the subject invention have been described in some detail, it is understood that obvious variations can be made without departing from the spirit and the scope of the invention as defined by the appended claims.

We claim:

1. A vaccine composition comprising:
    (a) an adjuvant composition comprising a *Polygala senega* saponin extract comprising at least one *P. senega* saponin capable of potentiating an immunological response, wherein said *P. senega* saponin extract is obtained from a *P. senega* L. plant;
    (b) a selected vaccine antigen; and
    (c) a pharmaceutically acceptable vehicle,
and further wherein said *P. senega* saponin extract comprises at least one saponin having the general structure:

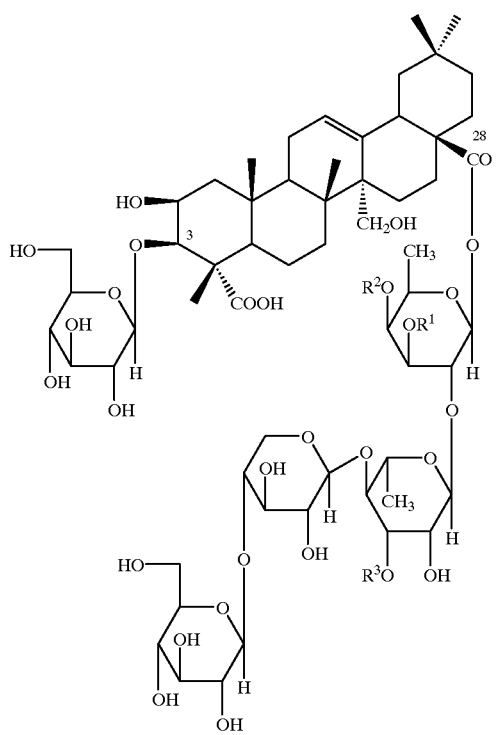

where $R^1$ is hydrogen; $R^2$ is selected from the group consisting of hydrogen, the E isomer of 4-methoxycinnamoyl, the Z isomer 4-methoxycinnamoyl, the E isomer of 3,4-dimethoxycinnamoyl, and the Z isomer of 3,4-dimethoxycinnamoyl; and $R^3$ is selected from the group consisting of hydrogen and β-D-apiofuranosyl.

2. The composition of claim 1, wherein said *P. senega* saponin extract is obtained by a method comprising:
    (a) providing roots of a *P. senega* L. plant;
    (b) extracting a crude saponin mixture from the roots with methanol;
    (c) extracting the crude mixture from (b) with n-butanol;
    (d) performing column chromatography on the butanolic extract; and
    (e) obtaining fractions from step (d) with hemolytic activity.

3. The composition of claim 1, wherein said *P. senega* saponin extract comprises senegin II.

4. A method for stimulating an immunological response in a vertebrate subject, said method comprising administering an effective amount of the composition of claim 1 to said subject.

5. A method for stimulating an immunological response in a vertebrate subject, said method comprising administering an effective amount of the composition of claim 2 to said subject.

6. A method for stimulating an immunological response in a vertebrate subject, said method comprising administering an effective amount of the composition of claim 3 to said subject.

7. A method of making a vaccine composition comprising combining an adjuvant composition comprising a *Polygala senega* saponin extract comprising at least one *P. senega* saponin capable of potentiating an immunological response, with a selected vaccine antigen, wherein said *P. senega* saponin extract is obtained from a *P. senega* L. plant, and further wherein said *P. senega* saponin extract comprises at least one saponin having the general structure:

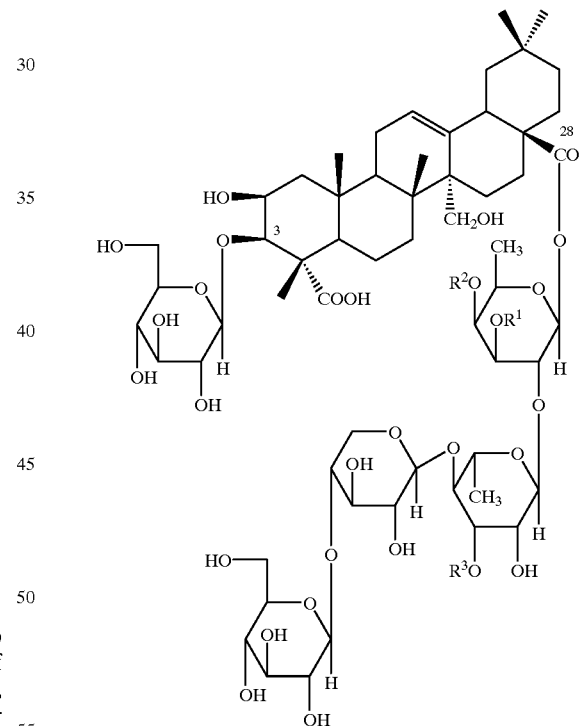

where $R^1$ is hydrogen; $R^2$ is selected from the group consisting of hydrogen, the E isomer of 4-methoxycinnamoyl, the Z isomer 4-methoxycinnamoyl, the E isomer of 3,4-dimethoxycinnamoyl, and the Z isomer of 3,4-dimethoxycinnamoyl; and $R^3$ is selected from the group consisting of hydrogen and β-D-apiofuranosyl.

8. The method of claim 7, wherein said *P. senega* saponin extract is obtained by a method comprising:

(a) providing roots of a *P. senega* L. plant;
(b) extracting a crude saponin mixture from the roots with methanol;
(c) extracting the crude mixture from (b) with n-butanol;
(d) performing column chromatography on the butanolic extract; and
(e) obtaining fractions from step (d) with hemolytic activity.

9. The method of claim 8, wherein the *P. senega* saponin extract comprises senegin II.

10. The method of claim 4, wherein said saponin extract and said antigen are administered separately.

11. The method of claim 4, wherein said *P. senega* saponin extract comprises senegin II.

* * * * *